United States Patent
Fangrow, Jr. et al.

(10) Patent No.: US 6,245,048 B1
(45) Date of Patent: Jun. 12, 2001

(54) MEDICAL VALVE WITH POSITIVE FLOW CHARACTERISTICS

(75) Inventors: Thomas F. Fangrow, Jr., Mission Viejo; Jonathan T. Schmidt, Newport Beach; Daniel J. Wait, Santa Ana; Dennis M. Bui, Orange, all of CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 09/078,941

(22) Filed: May 14, 1998

Related U.S. Application Data

(63) Continuation-in-part of application No. 08/767,587, filed on Dec. 16, 1996, now abandoned.

(51) Int. Cl.[7] .................................................. A61M 5/00
(52) U.S. Cl. ........................ 604/249; 604/246; 251/149.1
(58) Field of Search ................... 604/246, 249, 604/256, 523, 537, 284, 905, 533; 251/149.6, 149.1

(56) References Cited

U.S. PATENT DOCUMENTS

| | | |
|---|---|---|
| 2,756,740 | 7/1956 | Deane . |
| 3,965,910 | 6/1976 | Fischer . |
| 4,243,034 | 1/1981 | Brandt . |
| 4,804,015 | 2/1989 | Albinsson . |
| 5,049,128 * | 9/1991 | Duquette ................................ 604/83 |
| 5,147,333 | 9/1992 | Raines . |
| 5,201,717 | 4/1993 | Wyatt et al. . |
| 5,203,775 | 4/1993 | Frank et al. . |
| 5,221,271 | 6/1993 | Nicholson et al. . |
| 5,255,676 | 10/1993 | Russo . |
| 5,269,771 * | 12/1993 | Thomas et al. ......................... 604/213 |
| 5,306,265 | 4/1994 | Ragazzi . |
| 5,342,316 | 8/1994 | Wallace . |
| 5,348,542 | 9/1994 | Ellis . |
| 5,353,837 * | 10/1994 | Faust ................................ 137/614.18 |
| 5,380,306 * | 1/1995 | Brinon ................................ 604/244 |
| 5,407,437 | 4/1995 | Heimreid . |
| 5,417,673 | 5/1995 | Gordon . |
| 5,439,451 | 8/1995 | Collinson et al. . |
| 5,520,665 * | 5/1996 | Fleetwood .............................. 604/283 |
| 5,549,651 | 8/1996 | Lynn . |
| 5,603,706 | 2/1997 | Wyatt et al. . |
| 5,676,346 | 10/1997 | Leinsing . |
| 5,699,821 * | 12/1997 | Paradis ...................................... 137/1 |
| 5,730,418 * | 3/1998 | Feith et al. .......................... 251/149.6 |
| 5,749,861 * | 5/1998 | Guala et al. ............................ 604/249 |
| 5,882,348 * | 3/1999 | Winterton et al. ..................... 604/283 |
| 5,967,490 * | 10/1999 | Pike ..................................... 251/149.1 |
| 5,979,868 * | 5/2000 | Wu et al. ............................ 251/149.6 |
| 6,009,902 * | 1/2000 | Troiani et al. .................... 137/614.19 |
| 6,063,062 * | 5/2000 | Paradis ................................ 604/249 |

FOREIGN PATENT DOCUMENTS

| | | |
|---|---|---|
| 2175021 | 11/1996 | (CA) . |
| 670 955 A5 | 7/1989 | (CH) . |
| 0 263 789 | 4/1988 | (EP) . |
| 2 439 022 | 5/1980 | (FR) . |
| WO 97/31676 | 9/1997 | (WO) . |
| WO 98/26835 | 6/1998 | (WO) . |

* cited by examiner

Primary Examiner—Richard K. Seidel
Assistant Examiner—Cris Rodriguez
(74) Attorney, Agent, or Firm—Knobbe, Martens, Olson & Bear, LLP

(57) ABSTRACT

A medical valve device for use in selectively establishing a fluid flow between first and second medical implements is disclosed. The valve has a body defining a passage from a first port to a second port. The valve defines a first fluid volume when both medical implements are connected thereto, and a second, smaller volume when one of the implements is disconnected, thereby causing a positive flow of fluid from the valve to the second medical implement when the first implement is disconnected.

12 Claims, 25 Drawing Sheets

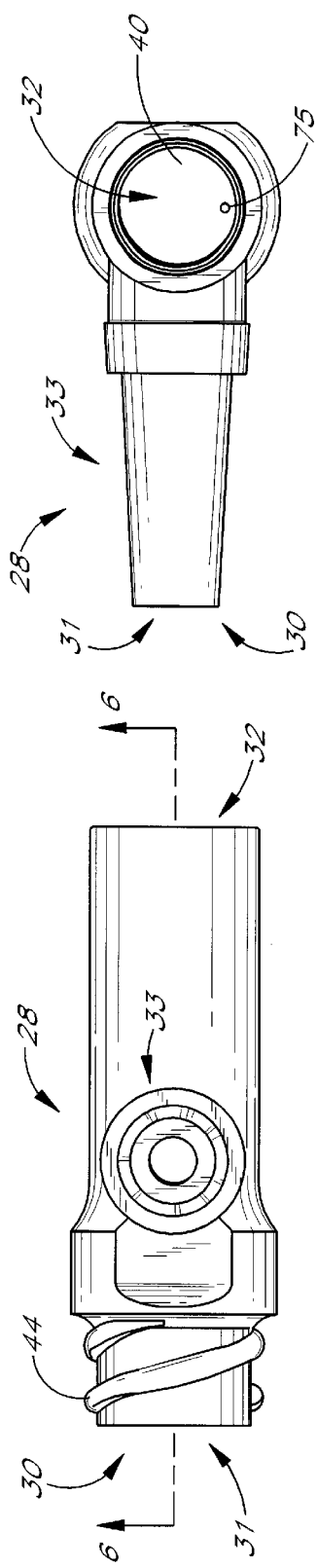
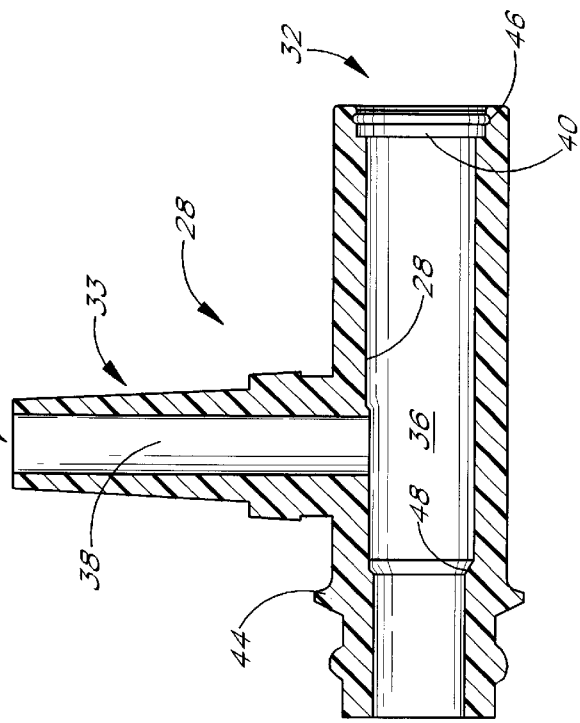
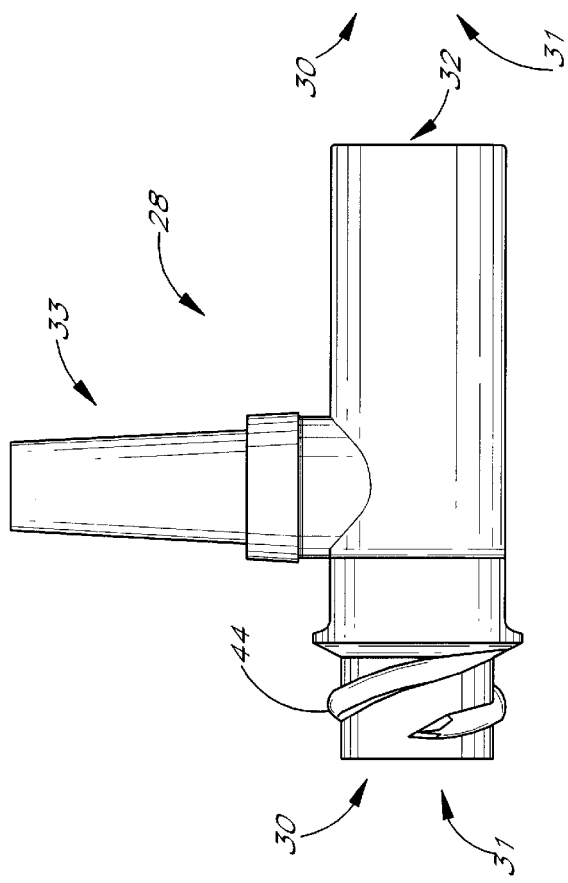

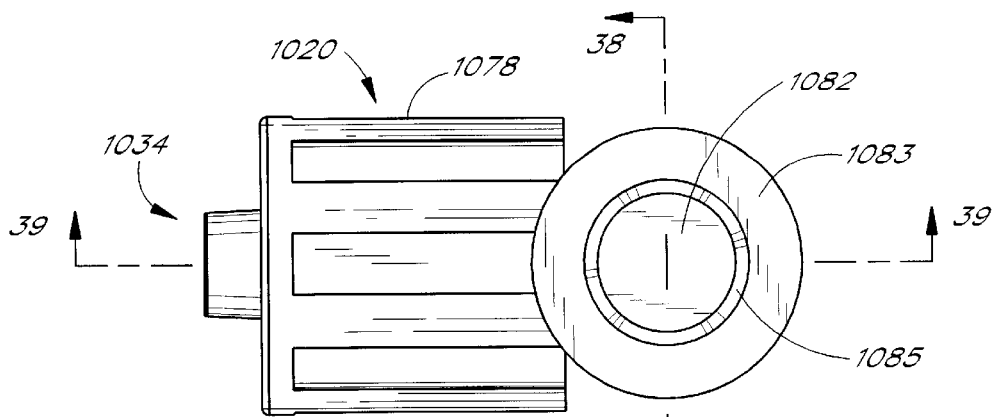
FIG. 37
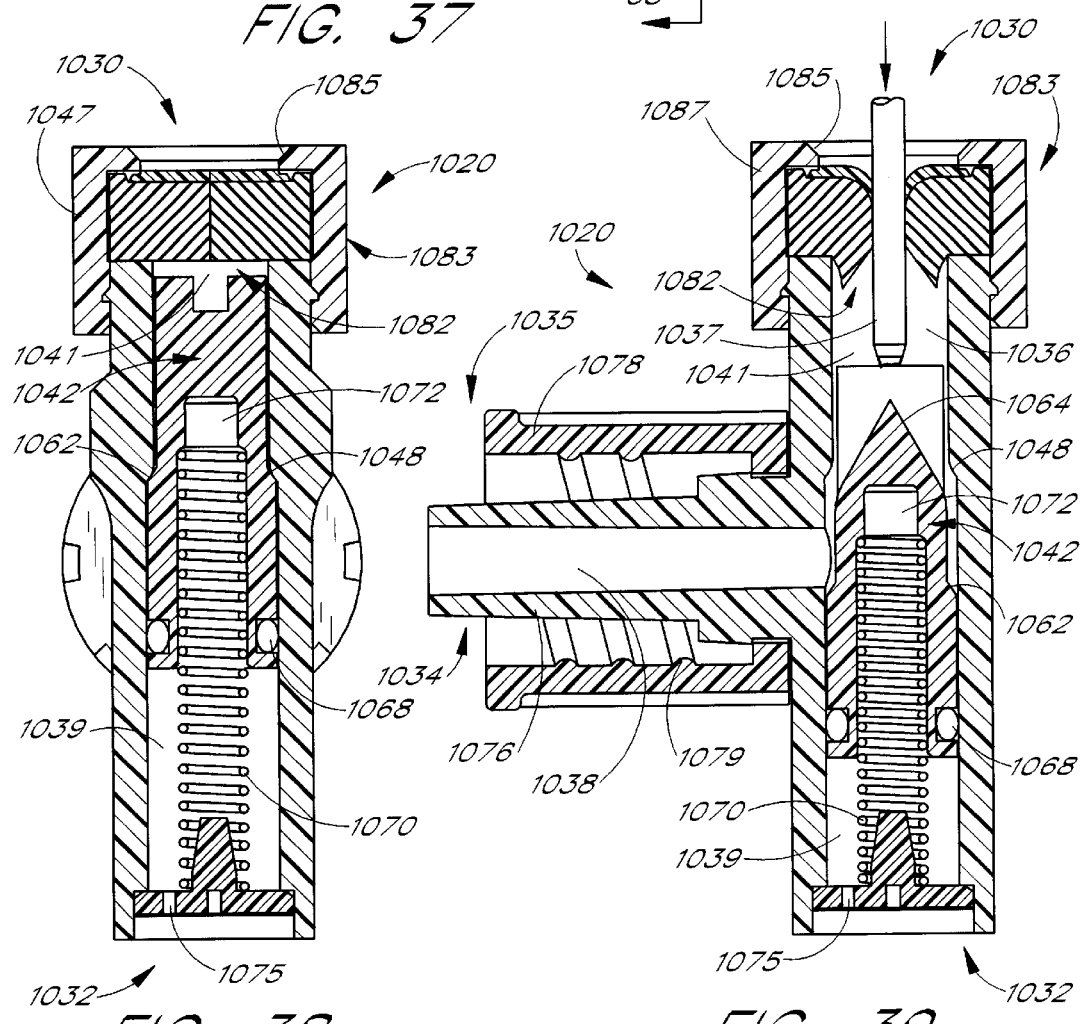
FIG. 38
FIG. 39

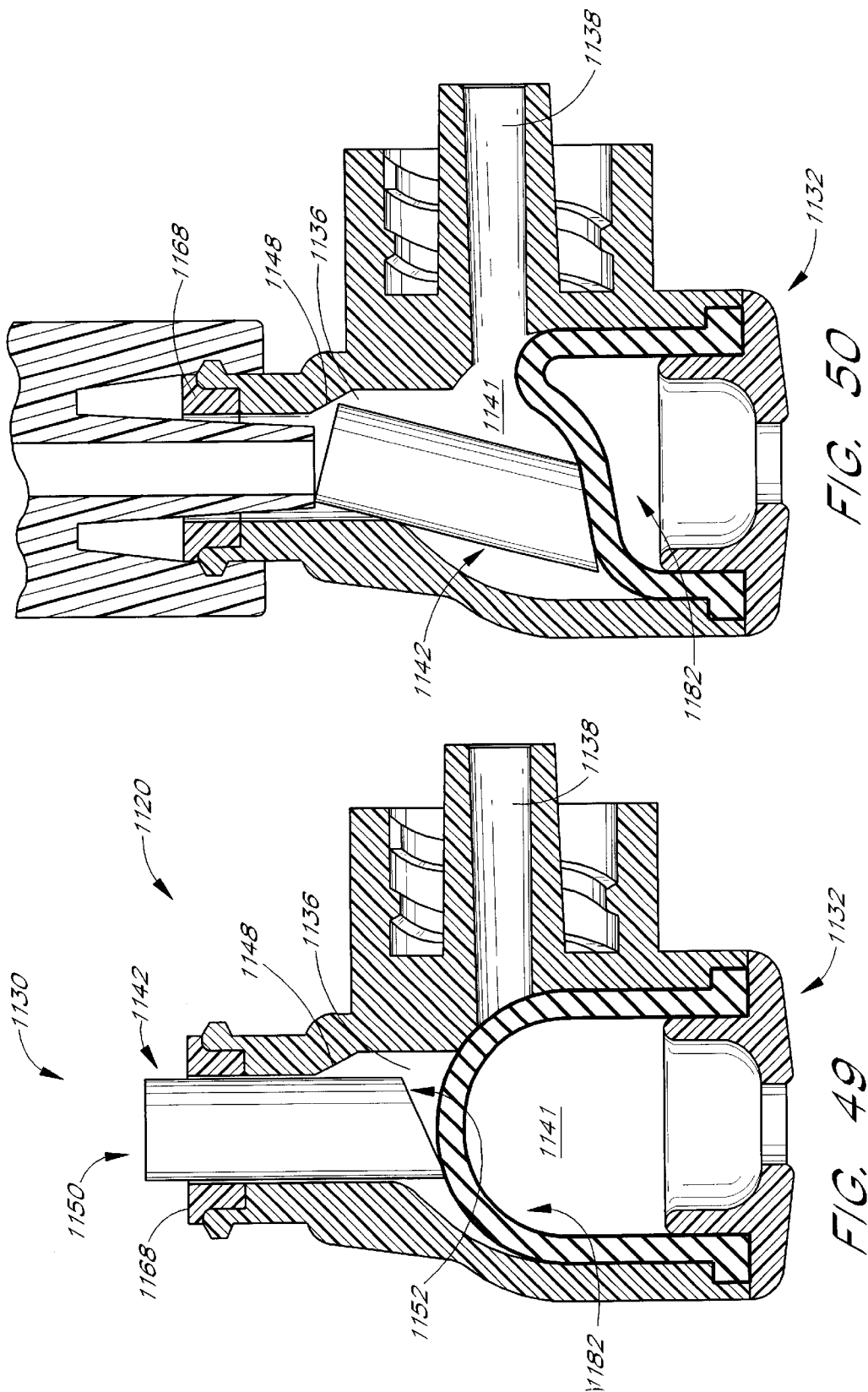

MEDICAL VALVE WITH POSITIVE FLOW CHARACTERISTICS

RELATED APPLICATIONS

This application is a continuation-in-part of U.S. patent application Ser. No. 08/767,587 filed Dec. 16, 1996 now abandoned.

FIELD OF THE INVENTION

This invention relates generally to a medical valve, and in particular to a valve which, when connected between a first medical implement, such as a fluid source, and a second medical implement, such as a catheter, facilitates fluid flow therebetween, and when the first medical implement is disconnected therefrom, induces a positive flow of fluid through the valve in the direction of the second medical implement.

BACKGROUND OF THE INVENTION

The manipulation of fluids for parenteral administration in hospitals and medical settings routinely involves the use of connectors and valves for selectively facilitating the movement of fluids between two points. These valves are typically placed along a fluid flow line leading to a patient or other destination. For example, the tube may lead to a catheter having its tip positioned within a patient.

The valve is arranged so that a fluid source or other line may be connected thereto for providing a fluid flow from the source to the patient. When the fluid source or line is removed, the valve closes, sealing the line leading to the patient.

The element which is connected to the valve may comprise a tube or other medical implement such as a conduit, syringe, IV set (both peripheral and central lines), piggyback line, or similar component which is adapted for connection to the medical valve. Unfortunately, prior art valves suffer from a problem arising from the disconnection of these medical implements from the valve.

These valves define a space within them through which a fluid or other material may flow from the implement to the line on which the valve is mounted. When the medical implement is connected to the valve, it typically occupies a portion of this internal valve space, displacing the fluid (whether it be a liquid or air) within the valve.

A problem arises when the medical implement is disconnected from the valve. When the implement is disconnected, it no longer occupies a portion of the space in the valve. The increase in space within the valve results in the fluid in the valve and line to which the valve is connected moving to fill the space. In effect, the removal of the implement creates a suction force which draws fluid into the valve.

In the medical setting, this movement of fluid is very undesirable. When the valve is connected to a fluid line leading to a patient, the movement of fluid through the line towards the space in the valve has the effect of drawing blood from the patient in the direction of the valve. A serious problem may result in that this blood may clot and clog the catheter near its tip, rendering it inoperable, and may even result in a clot of blood in the patient, which may prove fatal.

One attempt at overcoming this clogging problem has been to coat the inner surface of the catheter near its tip in order to prevent blood from sticking to its interior surfaces. This method has generally been unsuccessful in preventing clogging of the catheter.

The risk of blood clogging of the catheter is significantly heightened where the inner diameter of the catheter is small (e.g., 27 gauge). These small catheters have the advantage, however, that they reduce the trauma and discomfort caused by insertion into a patient. Because these catheters have a very small passage therethrough, even a small suction force may draw sufficient amount of fluid back through a catheter toward the valve to introduce blood into the catheter tip, which blood may clog the catheter's passage.

Overcoming the above-stated problem is made more difficult when considering other criteria which the valve must satisfy. For example, the valve should be arranged to so that it does not have any fluid stagnation points. If the fluid is allowed to stagnate in one or more areas of the valve, bacteria growth and other problems may occur.

In addition, the valve should have an internal flow path which is smooth. Sharp edges and corners may damage blood cells and cause hemolysis.

A valve which overcomes the above-stated problems is desired.

SUMMARY OF THE INVENTION

In accordance with the present invention there is provided a valve which is advantageously utilized between two medical implements. The valve of this invention has several features, no single one of which is solely responsible for its desirable attributes.

Most importantly, the valve is arranged to provide a positive flow (i.e. the movement of fluid in the direction out of the valve as opposed to into the valve) when one of the medical implements is disconnected therefrom. At the same time, the valve is safe, reliable and capable of being used repeatedly, is simple to manufacture and use, and is suitable for high pressure applications.

The valve of the present invention is particularly suited to use in an application where one of the medical implements comprises a catheter having its tip positioned in a patient. In a preferred embodiment the second medical implement comprises a fluid source having a connector for connection to the valve.

The valve of the present invention has a fluid space which expands upon connection of the second medical implement and contracts upon disconnection of the medical implement. When the valve is connected to a catheter, disconnection of the second medical implement creates a positive flow from the valve to the catheter tip upon disconnection of the medical implement to avoid the potential problems of blood-clogging. The valve is particularly suited for applications with a catheter where it is desirable to avoid negative flow, but may be used for other applications as well.

Preferably, the valve includes a housing adapted for connection to a first medical implement and a second medical implement. The valve defines a fluid space therein, and includes means for increasing the fluid space when the second medical implement is connected, and for decreasing the fluid space when the second medical implement is disconnected. Means are also preferably provided for defining a fluid path through the valve when both medical implements are connected thereto, and for closing the fluid path when the second medical implement is disconnected.

Further objections, features and advantages of the present invention over the prior art will become apparent from the detailed description of the drawings which follows, when considered with the attached figures.

BRIEF DESCRIPTION OF THE DRAWINGS

FIG. 3 is a top view of the housing illustrated in FIG. 2;

FIG. 4 is a side view of the housing illustrated in FIG. 2;

FIG. 5 is an end view of the housing illustrated in FIG. 2;

FIG. 6 is a cross-sectional side view of the housing illustrated in FIG. 2 and taken along line 6—6 therein;

FIG. 37 is a top view of the valve illustrated in FIG. 36;

FIG. 38 is a cross-sectional view of the valve illustrated in FIG. 37 taken along line 38—38 therein and illustrating a piston of the valve in a first position;

FIG. 39 is a cross-sectional view of the valve illustrated in FIG. 37 taken along line 39—39 therein and illustrating the piston of the valve in a second position;

FIG. 49 is a cross-sectional view of a valve in accordance with a twelfth embodiment of the present invention, illustrated with a seal thereof in a first position;

FIG. 50 is a cross-sectional view of the valve illustrated in FIG. 49 with the seal in a second position;

DETAILED DESCRIPTION OF THE PREFERRED EMBODIMENTS

Figure 1:
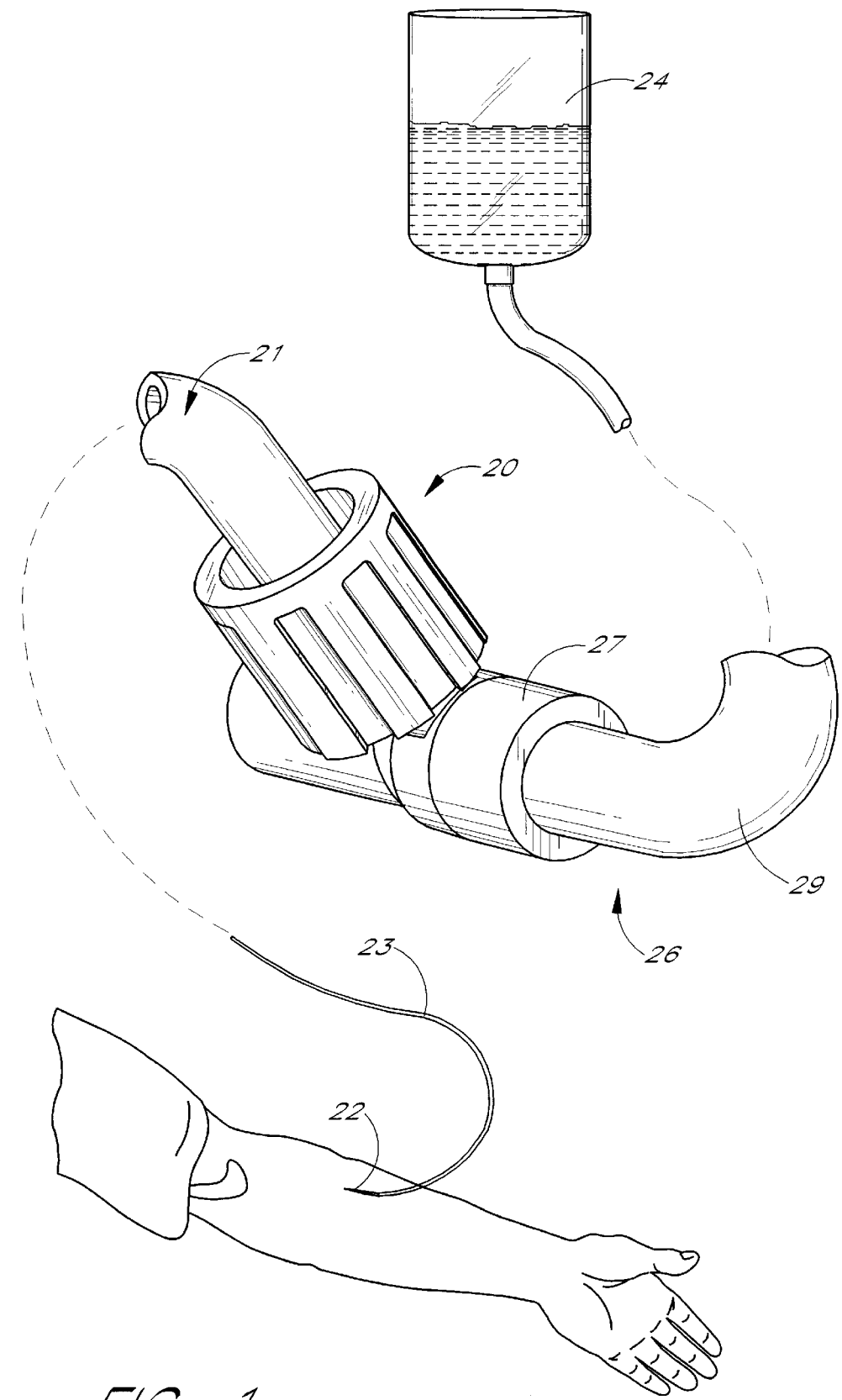
FIG. 1 illustrates a valve in accordance with the present invention as used to selectively provide fluid from a fluid source connected to a fluid line leading to a catheter which is inserted into a patient.
Figure 2:
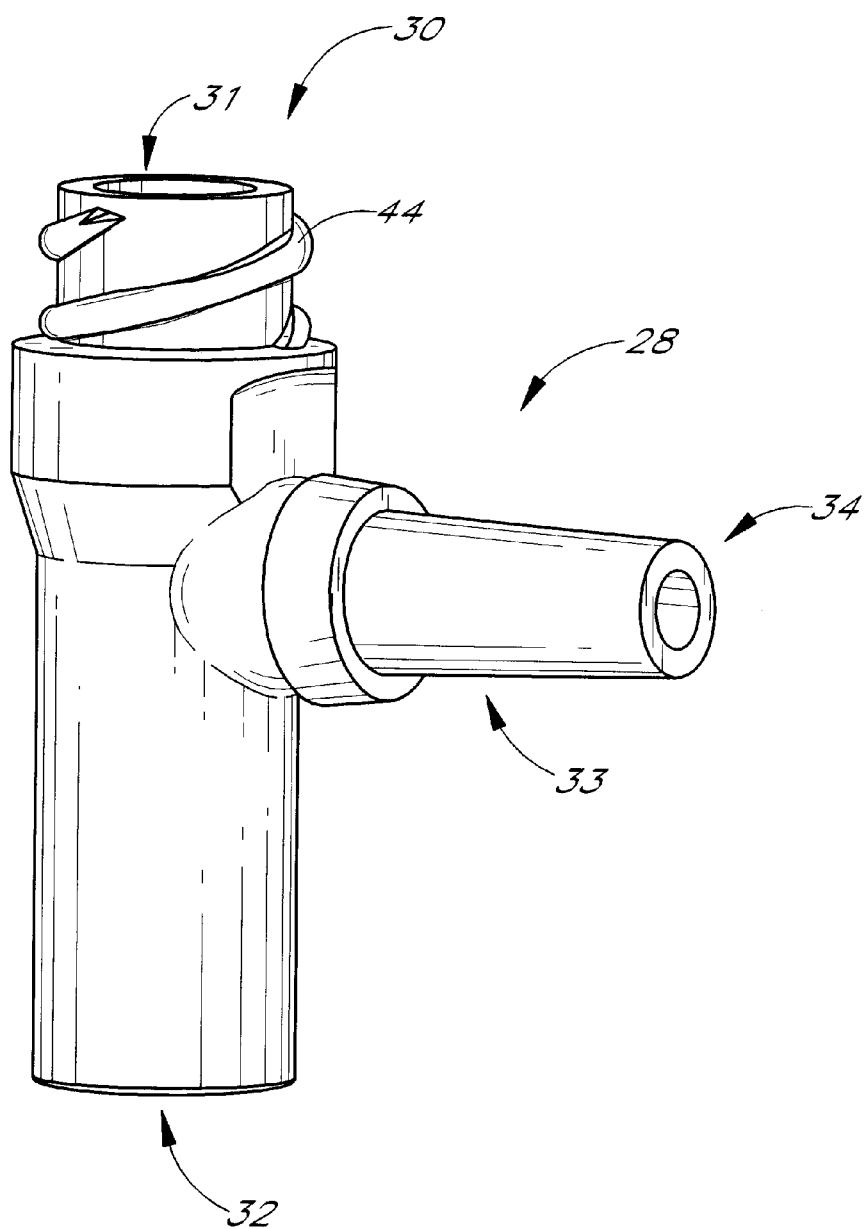
FIG. 2 is a plan view of a housing of the valve in accordance with a first embodiment of the present invention.

FIGS. 1–17 illustrate a valve 20 in accordance with a first embodiment of the present invention. FIG. 1 illustrates a particular use of the valve 20 to which the valve 20 is well suited. Of course, the valve 20 may be used in a variety of other manners.

As illustrated in FIG. 1, the valve 20 may advantageously be used to selectively control the flow of fluid to a catheter 22 from a fluid source 24 such as an I.V. bag. In this arrangement, a first medical implement 21 is connected to the valve 20. The first medical implement 21 comprises a tube 23 leading to a catheter 22. One end of the tube 23 is connected to the valve 20, and the catheter 22 has its tip positioned in a patient.

A second medical implement 26 is also connected to the valve 20. The second medical implement 26 comprises a connecting member 27 positioned at one end of a tube 29 which leads to the I.V. bag 24.

When so connected, the valve 20 permits fluid to flow from the I.V. bag 24 or other medical fluid source to the catheter 22 and into the patient. The valve 20 is also arranged so that when the second medical implement 26 is disconnected, fluid flow through the valve 20 is prevented. In addition, when the second medical implement 26 is disconnected, the valve 20 generates a "positive" fluid flow, i.e. flow of fluid in the direction of the patient, thereby preventing blood clogging of the catheter 22.

The first embodiment of the valve 20 of the present invention will now be described in more detail. As illustrated in FIGS. 2–6, the valve 20 includes a housing 28. The housing 28 is generally "T"-shaped, having a main portion with a first end 30 defining a first port 31 and having an opposing closed second end 32.

A branch 33 extends outwardly from the main portion of the housing 28. The branch 33 has a third end 34 defining a second or branch port 35. (See FIG. 7.)

Referring to FIG. 6, a main passage 36 is defined by an inner surface of a wall of the housing 28, and extends from the first end 30 to the second end 32 thereof. In addition, a branch passage 38 extends from the main passage 36 through the branch port to the third end 34.

As stated above, the second end 32 of the housing 28 is closed. Preferably, an end cap 40 is positioned in the second end 32 of the housing 28.

Figure 12:
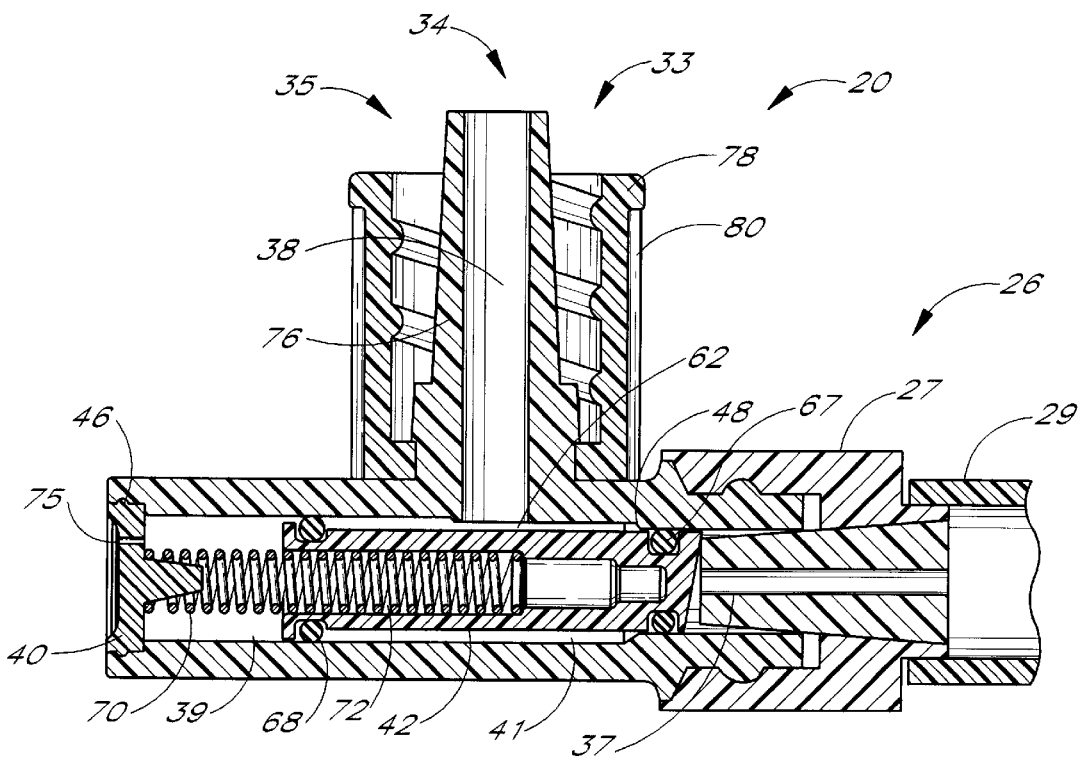
FIG. 12 is a cross-sectional view of the valve as illustrated in FIG. 11, with the piston in a second or compressed position utilizing the tip of a medical implement.
Figure 13:
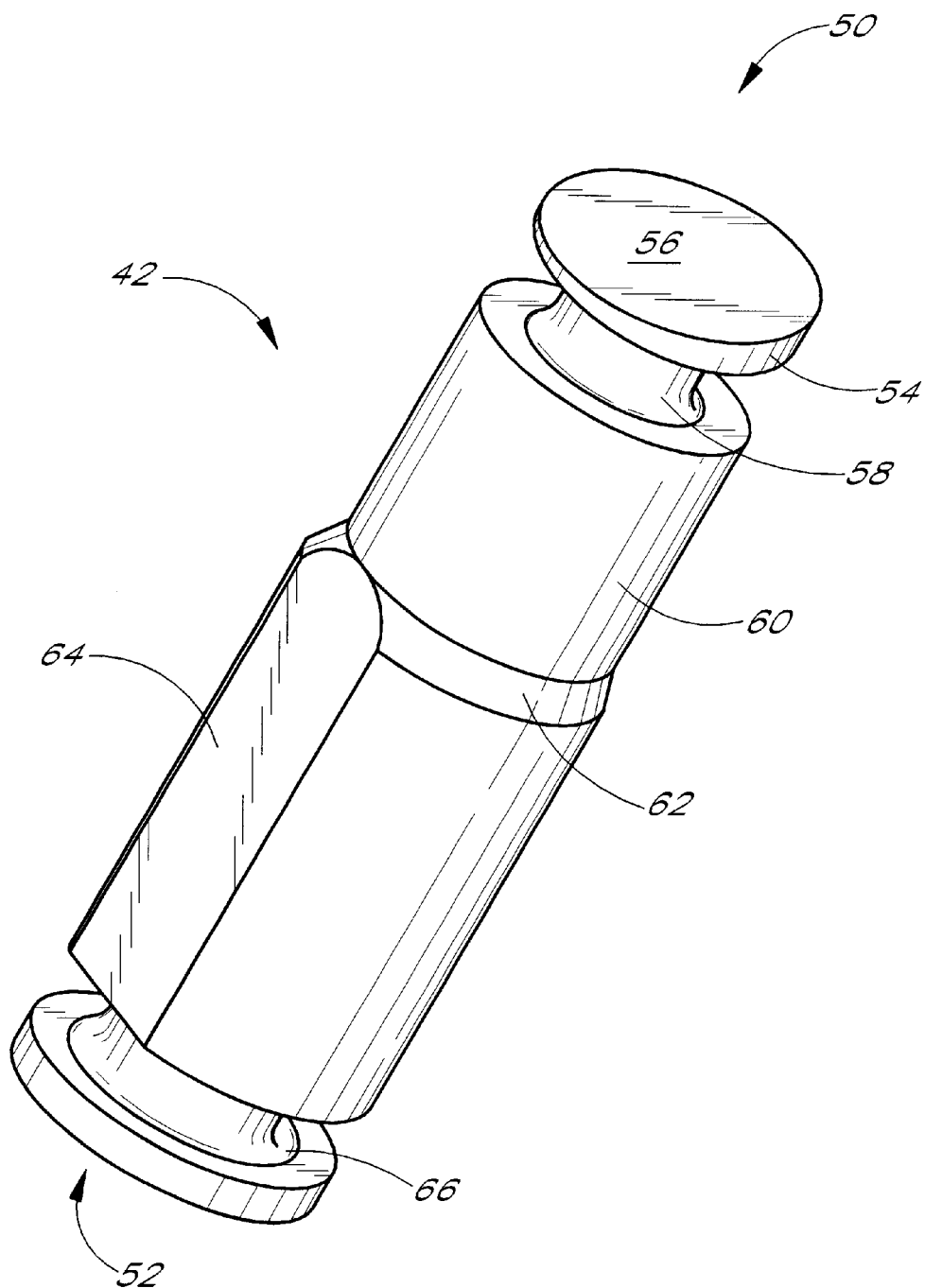
FIG. 13 is a perspective view of the piston of the valve of the first embodiment of the present invention.
Figure 14:
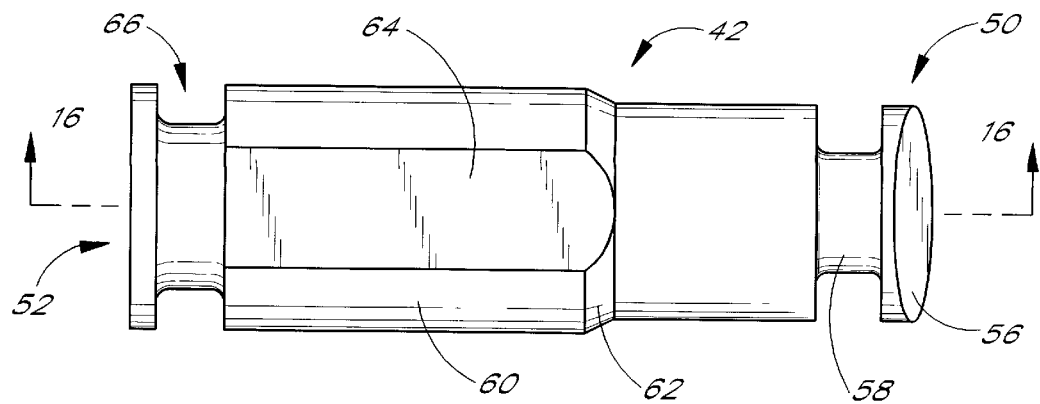
FIG. 14 is a top view of the piston illustrated in FIG. 13.
Figure 15:
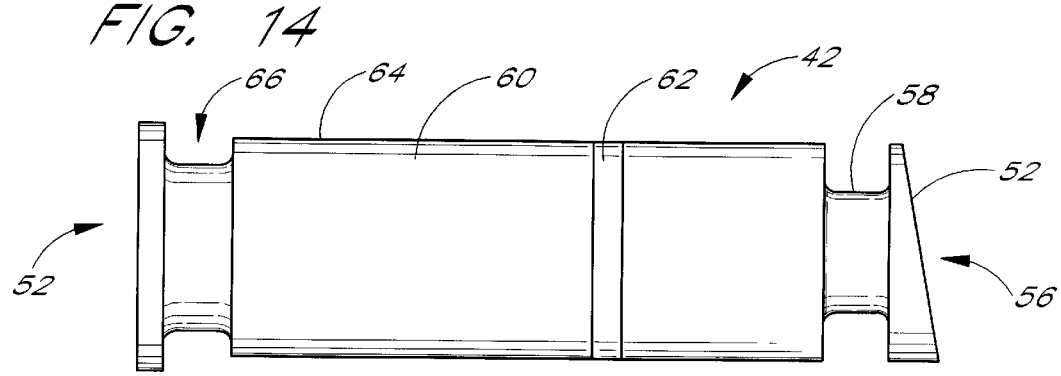
FIG. 15 is a side view of the piston illustrated in FIG. 13.
Figure 16:
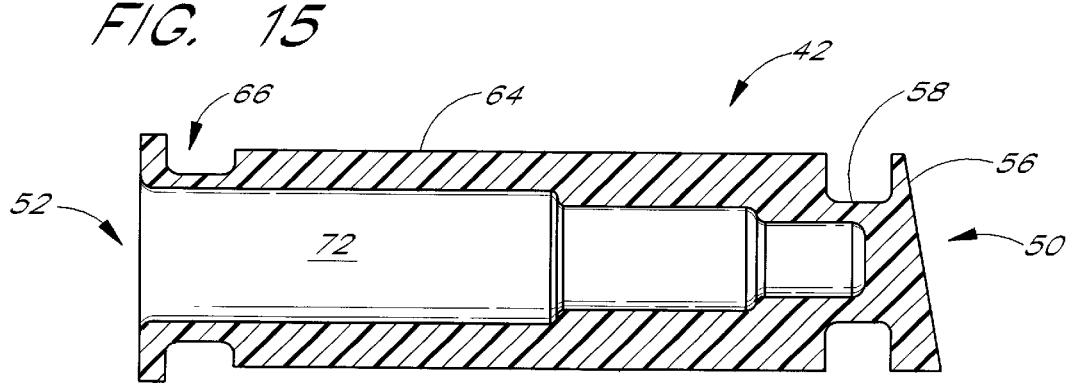
FIG. 16 is a cross-sectional side view of the piston illustrated in FIG. 14, taken along line 16—16 therein.
Figure 17:
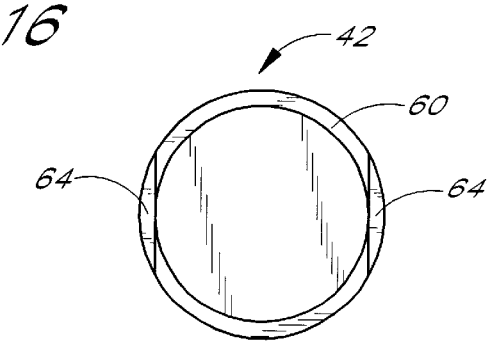
FIG. 17 is an end view of the piston illustrated in FIG. 14.

Excepting the branch portion 33, the housing 28 is generally cylindrical, as is the main passage 36. The first end 30 of the housing 28 is adapted to receive the cannula tip or nose 37 of an ANSI standard syringe, as illustrated in FIG. 12. As such, the passage 36 at the first end has a diameter larger than the nose of this type of syringe. It is, however, contemplated that the diameter of the passage 36 can be of any size to accommodate the attachment of other connector devices thereto.

Preferably, means are provided for locking the medical implement 26 to the first end 30 of the valve 20. In the preferred embodiment, threads 44 are positioned on the outer surface of the housing 28 at the first end 30 for mating engagement with threads on the connector 27 of the second medical implement 26. Other locking means known to those skilled in the art may be used instead of the threads 44.

As the main passage 36 is generally cylindrical, the end cap 40 is generally circular. The cap 40 engages the wall of the housing 28 at the second end 32 to close the passage. The end cap 40 preferably includes an outwardly extending tab 46 on its peripheral edge for engaging the inside surface of the housing 28 in the passage 36 for locking the end cap 40 in place.

For reasons described in more detail below, the diameter of the passage 36 at the first end 30 of the housing 28 is smaller than that at the second end 32. As illustrated, the passage 36 narrows (moving in a direction from the second towards the first end 32,30) near where the branch passage 38 extends from the main passage 36. In addition, the main passage 36 narrows again beyond the branch passage 38 near the first end 30. A circumferential ledge 48 is formed at that point where the main passage 36 narrows near the first end 32.

Figure 11:
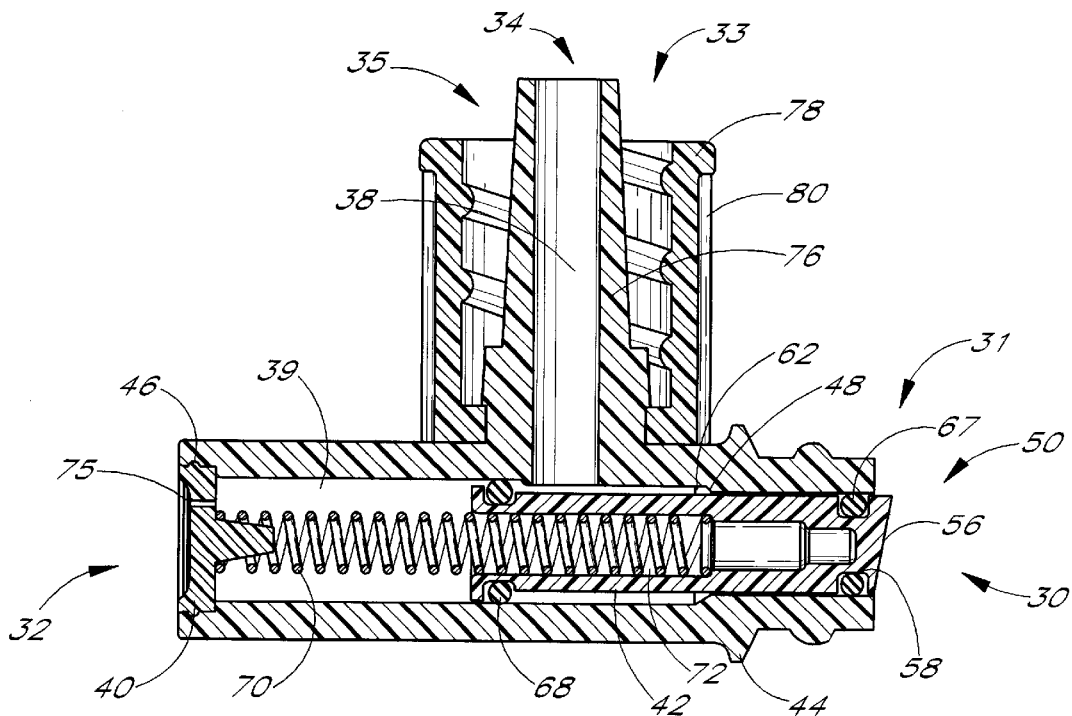
FIG. 11 is a cross-sectional view of the valve illustrated in FIG. 7, taken along line 11—11 therein, illustrating a piston of the valve in an uncompressed position.

As illustrated in FIGS. 11 and 12, a piston 42 is slidably positioned within the main passage 36. Referring to FIGS. 13–17, the piston 42 is generally cylindrical, having a maximum outer diameter which is just slightly smaller than the maximum diameter of the passage 36. The piston 42 has a first end 50 and a second end 52 and a length from end to end which is less than the distance from the first end 30 to the second end 32 of the housing 28.

The piston 42 has a head 54 at its first end 50. As illustrated, the head 54 is circular in outer shape, but has a slanted end surface 56. A neck 58 extends from the head 54 to a body 60. The neck 58 preferably has a reduced diameter as compared to the head 54. An "O"-ring 67 or similar seal is positioned around the reduced diameter neck 58 for engagement with the adjacent wall of the housing 28.

A first portion of the body 60 adjacent the neck 58 has a smaller diameter than a second portion of the body 60 positioned nearer the second end 52. The transition between these two sections creates a shoulder 62. The shoulder 62 is arranged to engage the ledge 48 in the passage 36 of the housing, preventing removal of the piston 42 from the first end 30 of the housing 28.

A pair of elongate cut-outs or depressions 64 are formed on opposite sides (i.e. 180 degrees from one another) in the second portion of the body 60 of the piston 42. The cut-outs 64 are trough shaped, and extend inwardly to a radial depth which is equal to the height of the shoulder 62 (so that the bottom of the cut-out is at the same level as the exterior of the housing at the first portion of the body).

A groove 66 is formed in the piston 42 near its second end 52. Preferably, a seal 68 (see FIGS. 11 and 12) is positioned in this groove 66. The seal 68 is preferably an "O"-ring comprised of rubber or a similar resilient, sealing material.

In the preferred embodiment, the piston 42 is hollow, having a recessed area therein. As illustrated, the recessed area comprises a bore or passage 72 extending inwardly from the second end 52 thereof. The bore 72 preferably has three diameters, the largest of which is near the second end 52, and tapering in diameter in two steps to two other diameters which are less than the first. The bore 72 is in communication with the passage 36 within the housing 28. The bore 72 preferably has the three diameters so that the wall of the housing 28 has a generally uniform thickness, which facilitates molding. Those of skill in the art will appreciate that the bore 72 may have more or less than three different diameters.

The assembled valve 20, wherein the piston 42 is positioned in the housing 28, is illustrated in FIGS. 7–12. As illustrated, the seal 68 divides the main passage 36 into a first cavity or chamber 39 and a second cavity or chamber 41. The first chamber 39 comprises the space between the end cap 40 and the second end 52 of the piston 42, as well as the space defined within the piston 42 by the bore 72. The second chamber 41 is that space from the seal 68 to the first end 30 of the housing 28 not occupied by the piston 42.

As illustrated in FIGS. 11 and 12, the piston 42 is moveable from a first or "uncompressed" position in which the shoulder 62 engages the ledge 48 and the first end 50 of the piston 42 extends outwardly of the first end 30 of the housing 28, to a second or "compressed" position in which the piston 42 is moved in the direction of the second end 32 of the housing 28.

Means are provided for biasing the piston 42 into its first position. Preferably, this means comprises a spring 70. The spring 70 is of the helical variety, and has its first end engaging the cap 40 and its second end engaging the piston 42, preferably inside the bore 72 at a ledge created at a change in diameters thereof.

The first chamber 39 is air filled. In order to accommodate the movement of the piston 42 towards the second end 32 of the housing 28, an air vent 75 is preferably provided through the end cap 40 (see also FIG. 5). The air vent 75 is a passage through the cap 40 from the chamber 39 to the exterior of the valve 20 which allows air to flow into and out of the chamber 39.

The branch 33 extends generally perpendicularly from the remainder of the housing 28 between its first and second ends 30,32. The branch 33 is generally defined by a cylindrical wall 76 extending outwardly from the wall which defines the main portion of the housing 28. The wall 76 defines the branch passage 38.

Figure 7:
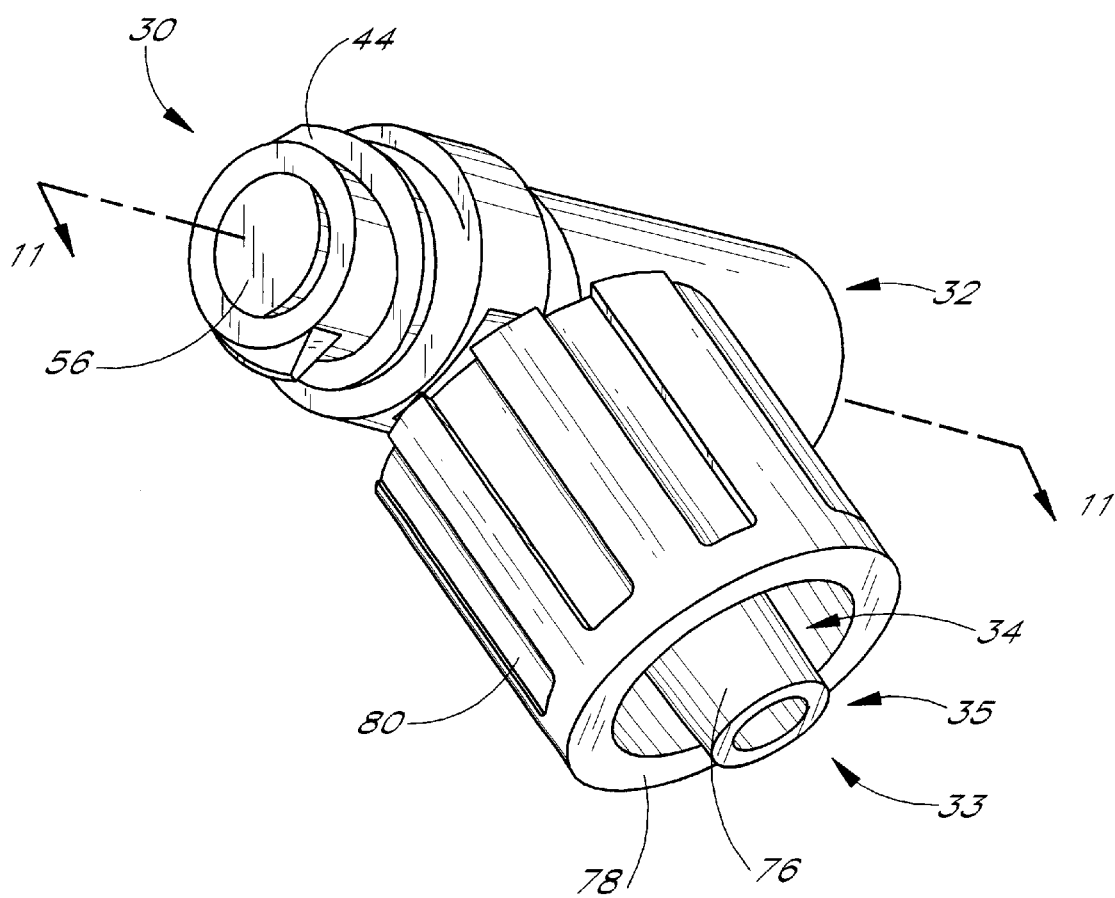
FIG. 7 is a perspective view of the valve in accordance with the first embodiment of the present invention.
Figure 8:
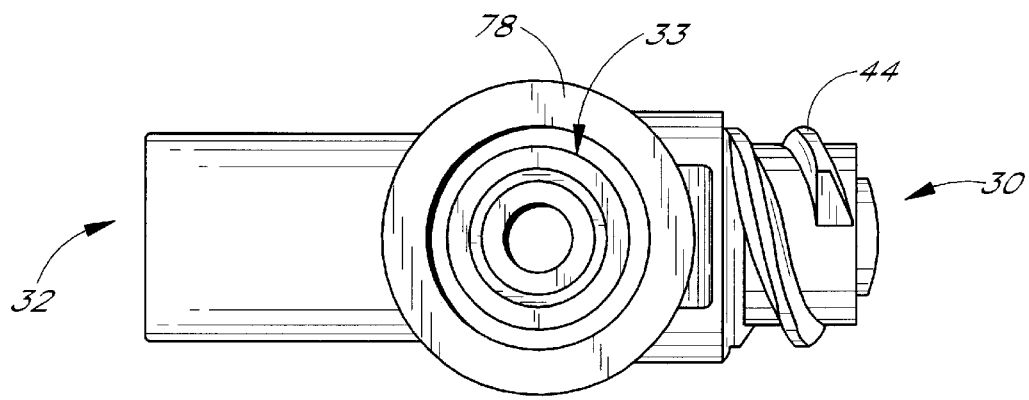
FIG. 8 is a top view of the valve illustrated in FIG. 7.
Figure 9:
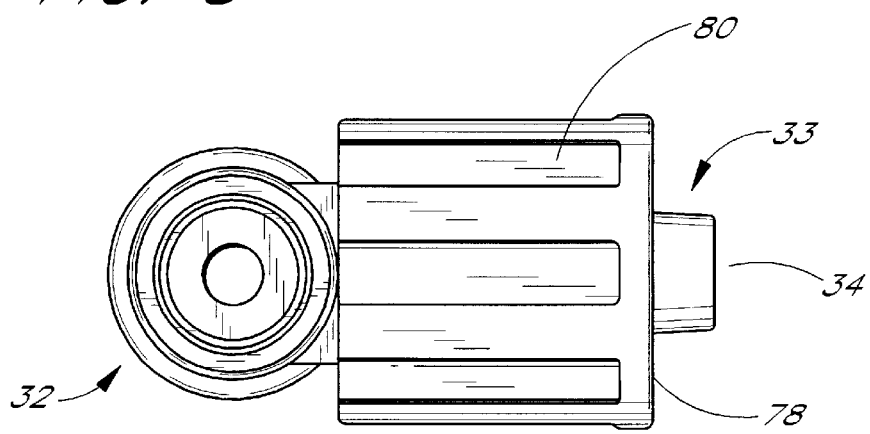
FIG. 9 is a first end view of the valve illustrated in FIG. 7.
Figure 10:
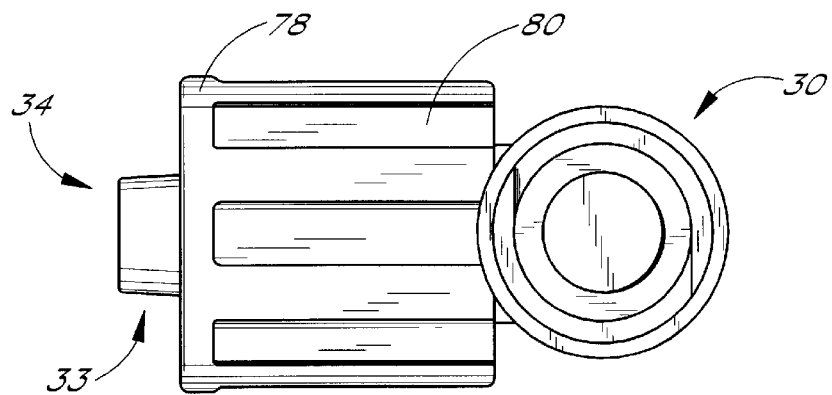
FIG. 10 is an opposite end view of the valve illustrated in FIG. 9.

As best illustrated in FIGS. 7 and 11–12, a threaded sleeve 78 preferably extends about the branch of the housing 28. The sleeve 78 has an inner diameter which is larger than the outer diameter of the wall 76. In fact, the inner diameter is large enough to define a space between the wall 76 and sleeve 78 in which the end of a tube or other member may be inserted.

The sleeve 78 is preferably connected to the wall 76. As illustrated in FIG. 7 and 9–12, the outer surface of the sleeve 78 has a number of recesses 80 therein for aiding in gripping by a user.

The operation of the valve 20 will now be described in detail with reference to the figures. A user first connects the first medical implement 21 to the branch port 35 at the third end 34. When the first medical implement 21 is of the type disclosed above, an end of the tube 23 having a connector thereon is guided over the wall 76 between the outside of the wall and the inside of the sleeve 78. The connector is preferably threaded into engagement with the sleeve 78 to retain it in place.

The user then engages the second medical implement 26 to the first port 31 of the valve 20. Preferably, the medical implement has a blunt cannula tip 37 positioned within a connector 27 having a mating locking structure to the threads 44 or other locking means positioned on the housing 28.

The user advances the cannula tip 37 until it engages the end surface 56 of the piston 42. As the user further advances the implement, the piston 42 is pressed in the direction of the second end 32 of the housing 28, compressing the spring 70. Air within the passage 36 between the end cap 40 and the piston 42 and within the bore 72 of the piston is forced out through the vent 75 in the end cap 40.

Once the connector 27 of the implement 26 extends about the first end 30 of the housing 28, the user locks the connector 27 to the housing 28 to provide a secure connection. So engaged, the implement 26 is connected to the valve 20 in the position illustrated in FIG. 12.

When the piston 42 is in this position, a fluid flow path is established from the second medical implement 26 (and through the tube 29 from the I.V. bag 24 in the arrangement illustrated in FIG. 1) through the valve 20 to the first medical implement 21 (and thus through the catheter 22 to the patient). Fluid flows through the tip 37 of the cannula along the first end 54 of the piston 42 into the second chamber 41, i.e. that space between the piston 42 and the inner surface of the housing 28, including the space within the cut-outs 64. The total volume of fluid within the valve 20 when the second medical implement is attached and fluid fills the second chamber 41 is an amount V1.

Fluid is prevented from travelling beyond the second end 52 of the piston 42 into the first chamber 39 by the seal 68. As a result, the fluid flowing from the second medical implement 26 towards the valve 20 is forced to flow into the branch passage 38 and thereon into the tube 23 to the patient.

Most importantly, when the second medical implement 26 is disconnected from the valve 20, the valve 20 causes fluid to flow in the direction of the first medical implement through the branch passage 38. As the second medical implement 26 is disconnected, the spring 70 forces the piston 42 towards the first end 30 of the housing 28. As the piston 42 moves in this direction, the piston 42 slides through the narrowest portion of the passage 36 near the first end 30 of the housing 28. This movement causes the total volume or fluid space in the second chamber 41 between the piston 42 and the housing 28 to reduce. Once the shoulder 62 of the piston 42 hits the ledge 48, the piston stops moving, and the fluid volume within the valve 20 is at a minimum amount V2.

Because the fluid volume in the valve 20 decreases as the second medical implement 26 is disconnected, some fluid within the housing 28 must be displaced. This fluid moves along the troughs 64 and into the branch passage 38 in the direction of the patient, the total volume of fluid flowing in the "positive" direction $V_D$ (volume displaced) being equal to the difference between the maximum volume V1 less the minimum volume V2.

Once the piston 42 has reseated, the valve 20 prevents later flow of fluid from the first medical implement 21 back through the valve 20, since the piston closes off the passage 36 near the first end 30 of the housing 28. This prevents, for example, the blood pressure of the patient from forcing blood back to the valve 20 and out the first port 31.

Besides providing a positive flow, the valve 20 of the present invention has several other distinct advantages. First, it is often the case that medical valves have a fluid containing area within them in which the fluid may stagnate. Fluid stagnation is undesirable, as it may result in bacteria growth and similar problems.

The valve 20 of the present invention has its fluid containing area between the piston 42 and the wall of the housing 28 which defines the main passage 36. This generally annular space is flushed each time fluid is injected from the top end 50 of the piston 42.

Another aspect of the present invention is that the end surface 56 of the first end 50 of the piston 42 is smooth. This allows a user of the valve 20 to swab the cannula engaging surface before connecting the medical implement to the first port 31 of the valve. The swabbing may be with alcohol or a similar disinfectant which serves to prevent the entry of bacteria and the like into the fluid system through the valve 20.

It may now be understood that the valve 20 includes both means for reducing the fluid volume or space therein when the second medical implement 26 is disconnected (i.e., in this case, a reduction in the volume of chamber or cavity 41), and means for establishing a flow path through the valve 20 when the second medical implement 26 is connected and for closing this fluid path when the implement is disconnected. In this first embodiment, these means are provided by the single piston 42.

Figure 18:
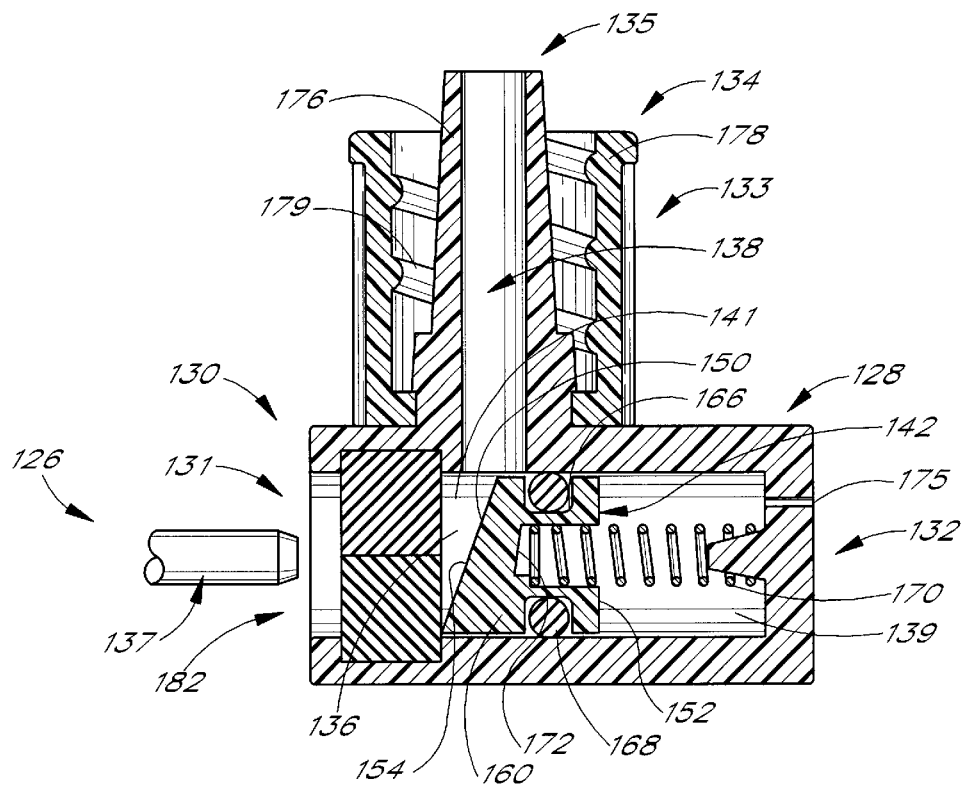
FIG. 18 is a cross-sectional side view of a valve in accordance with a second embodiment of the present invention, illustrating a piston of the valve in a first position.
Figure 19:
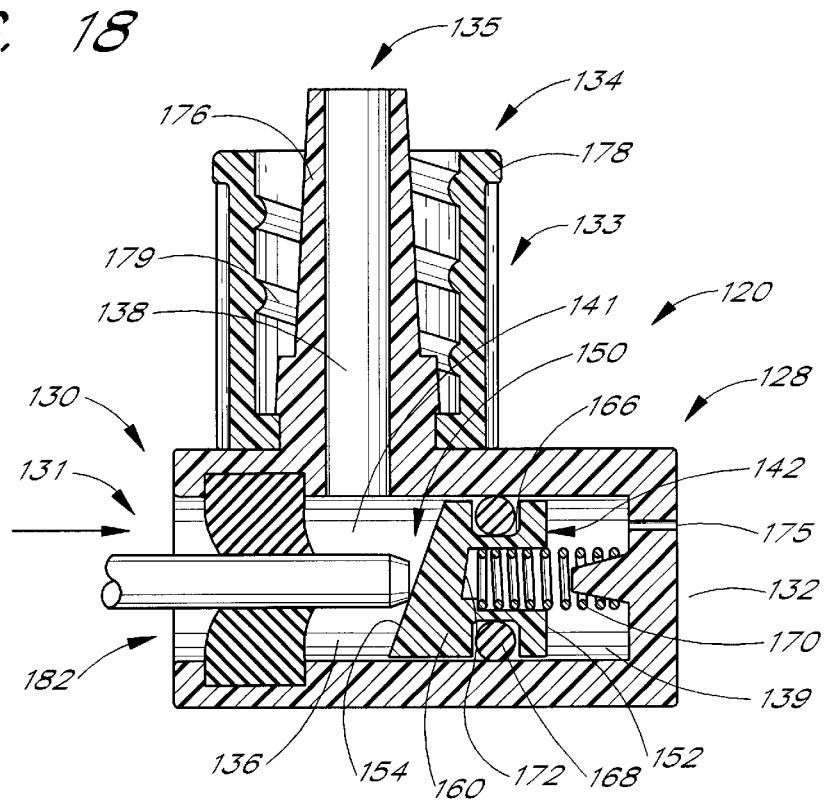
FIG. 19 is a cross-sectional side view of the valve as illustrated in FIG. 18, with the piston in a second position.

A second embodiment valve 120 in accordance with the present invention is illustrated in FIGS. 18 and 19. As illustrated, this valve 120 includes a housing 128 which is similar to the housing of the valve 20 described above, except that this housing is shorter in length between a first end 128 and a second end 130, as a piston 142 of the valve 120 is also shorter.

As illustrated, the first end 130 defines a first port 131, and the opposing second end 132 is closed. A branch 133 extends to a third end 134 defining a branch port 135.

A main passage 136 extends from the first end 130 towards the second end 132 of the housing. The main passage 136 is defined by an inner surface of a wall of the housing 128. The main passage 136 is generally cylindrical in shape, in this embodiment having no ledges or steps.

A branch passage 138 extends perpendicularly from the main passage 138 between the first and second ends 130,132 of the housing 128. The branch passage 138 is preferably defined by a wall 176. The branch passage 138 is generally cylindrical in shape.

The piston 142 is movably positioned within the passage 136 of the housing 128. The piston 142 has a body 160 which is generally cylindrical in shape, and has a first end 150 and a second end 152. The first end 150 defines a head 154 having a slanted surface. In this embodiment, the piston 142 is similar to that of the first embodiment, except the piston is much shorter and does not have the differing diameter sections.

A groove 166 is formed in the body 160 between its first and second ends 150,152. As illustrated, a seal 168 is positioned in the groove 166 of the piston 142. This seal 168 divides the passage 136 in the housing 128 into a first chamber 139 and a second chamber 141.

A recess or bore 172 is formed in the body 160 of the piston 142 extending from the second end 152. A first end of a spring 170 is positioned in the recess 172 and extends therefrom to the second end 132 of the housing 128 for biasing the piston 142 towards the first end 130 of the housing 128.

A vent 175 is provided through the second end 132 of the housing 128. The vent 175 permits air to flow between the first chamber 139 and the outside of the housing 128.

A resilient, pre-slit seal 182 is provided near the first end 130 of the housing 128. The seal 182 is generally circular for fitting within the passage 136, and preferably includes a pre-formed slit 184 through which the tip of a medical implement may pass. The seal 182 is preferably constructed of a resilient material such that it naturally returns to the position (i.e. reseals) illustrated in FIG. 18, where the slit 184 is closed and fluid is prevented from passing therethrough.

As with the first embodiment, a sleeve 178 is positioned about the wall 176 defining branch 133 of the housing 128. The sleeve 178 preferably has threads 179 on an inner surface thereof.

The operation of the valve 120 will now be described in detail with reference to FIGS. 18 and 19. A user first connects the first medical implement (not shown, but which may be similar to that illustrated in FIG. 1) to the branch port 135 at the third end 134. When the first medical implement is of the type disclosed above, the free end of the tube is guided over the wall 176 between the outside of the wall and the inside of the sleeve 178.

The user then engages the second medical implement 126 to the first port 131 of the valve 120. Preferably, the medical implement has a blunt cannula tip 137.

The user advances the cannula tip 137 until it engages the end surface 156 of the piston 142. As the user further advances the implement, the piston 142 is pressed in the direction of the second end 132 of the housing 128, compressing the spring 170. Air within the first chamber 139 between the end cap 140 and the piston 142 and within the bore 172 of the piston is forced out through the vent 175 in the end cap 140.

When the piston 142 is in this position (as illustrated in FIG. 19), a fluid flow path is established from the second medical implement 126 (such as through a tube from an I.V. bag) through the valve 120 to the first medical implement (and thus through the catheter to the patient). Fluid flows through the tip 137 of the cannula along the first end 154 of the piston 142 into the second chamber 141. The total volume of fluid within the valve 120 when the second medical implement is engaged and fluid fills the second chamber 141 is an amount V1.

Fluid is prevented from travelling beyond the seal 168 into the first chamber 139. As a result, the fluid flowing from the second medical implement 126 into the second chamber 141 is forced to flow into the branch passage 138 and thereon into the tube to the patient.

Most importantly, when the second medical implement 126 is disconnected from the valve 120, the valve 120 causes fluid to flow in the direction of the first medical implement through the branch passage 138. As the second medical implement 126 is disconnected, the spring 170 forces the piston 142 towards the first end 130 of the housing 128. This movement causes the total volume or fluid space in the second chamber 141 between the piston 142 and the seal 182 at the first end 130 of the housing 128 to reduce. Once the piston 142 encounters the seal 182, the piston stops moving, and the fluid volume within the valve 120 is at a minimum amount V2.

Because the fluid volume in the valve 120 decreases as the second medical implement 126 is disconnected, some fluid within the housing 128 must be displaced. This fluid moves through the branch passage 138 in the direction of the patient, the total volume of fluid flowing in the "positive" direction being equal to the difference between the maximum volume V1 less the minimum volume V2.

Once the implement tip 137 is removed, the valve 120 prevents later flow of fluid from the first medical implement back through the valve 120, since the slit 184 in the seal 182 reseals, closing off the passage 136 near the first end 130 of the housing 128.

Besides providing a positive flow, the valve 120 of the present invention has other advantages. Again, the valve 120 of this embodiment has its fluid containing area between the piston 142 and the housing 128 which defines the main passage 136. This space is flushed each time fluid is injected from the top end 150 of the piston 142.

Advantageously, a needle may be used to penetrate the seal 182 instead of the blunt tip cannula 137. In this arrangement, the seal 182 is preferably resilient so that it reseals, but need not be pre-slit.

As may now be understood, the means for selectively establishing the fluid flow path through the valve 120 and the means for causing a reduction in fluid space in the valve 120 when the second medical implement 126 is removed are separate in this embodiment. In this embodiment, the means for selectively establishing the fluid flow path comprises the seal 184, while the means for reducing the fluid space comprises the biased piston 142.

Figure 20:
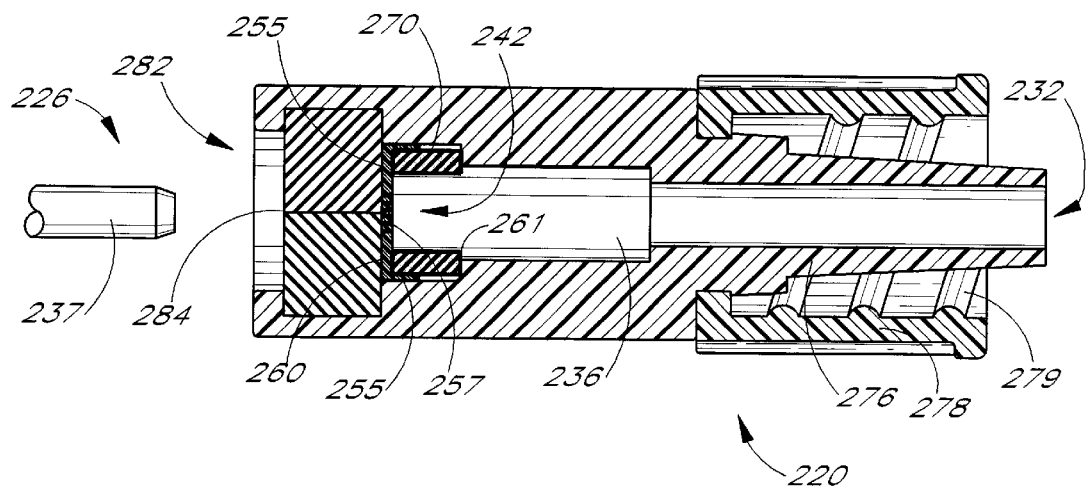
FIG. 20 is a cross-sectional side view of a valve in accordance with a third embodiment of the present invention, illustrating a piston of the valve in a first position.
Figure 21:
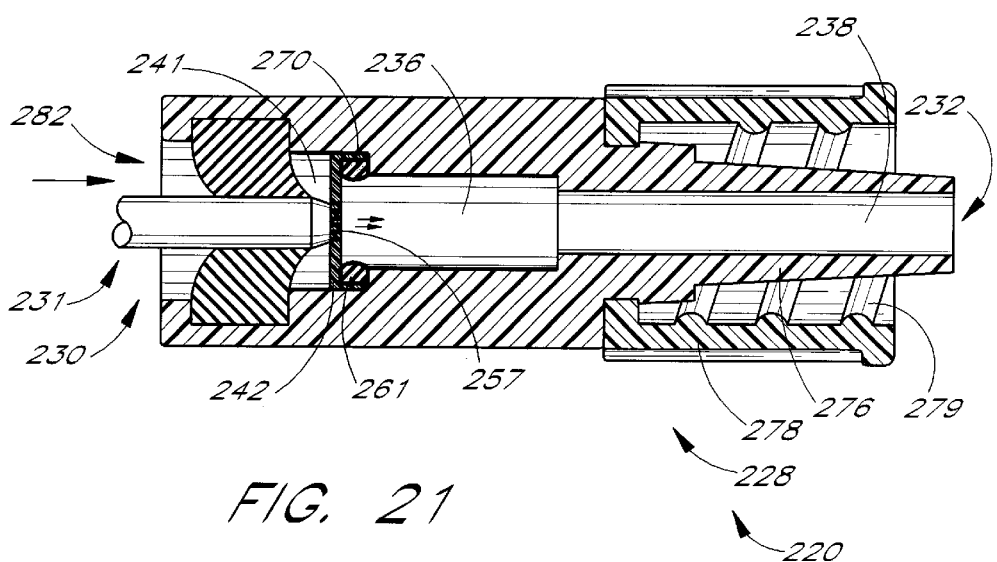
FIG. 21 is a cross-sectional side view of the valve as illustrated in FIG. 20, with the piston in a second position.

A third embodiment valve 220 in accordance with the present invention is illustrated in FIGS. 20 and 21. As illustrated, this valve 220 includes a housing 228. As illustrated, the housing 228 is a generally cylindrical body having a first end 230 defining a first port 231 and having an opposing second end 232.

A main passage 236 extends from the first end 230 towards the second end 232 of the housing. The main passage 236 is defined by an inner surface of the housing 228. The main passage 236 is generally cylindrical in cross-section. An extension passage 238 of smaller diameter extends from the main passage 238 to the second end 232 of the valve 220, the passage 238 being defined partly by a wall 276. A sleeve 278 is positioned about the outside of the wall 276. The sleeve 278 preferably has threads 279 on an inner surface thereof.

The piston 242 is movably positioned within the passage 236 of the housing 228. The piston 242 has a body 260 having a generally circular first end 250 or head. A flange or skirt 255 extends outwardly from a circumference of the head 250. A number of passages 257 are provided through the head 250 of the piston 242.

A biasing member 270 is positioned between the piston 242 and a ledge 261 formed by the wall of the housing 238 at the intersection of two portions of the passage 236 having differing diameters. The biasing member 270 is preferably an annular, compressible and generally close-cell material, such as foam or the like.

A resilient, pre-slit seal 282 is provided near the first end 230 of the housing 228. The seal 282 is generally circular for fitting within the passage 236, and includes a pre-formed slit 284 through which the tip of a medical implement may pass. The seal 282 is preferably constructed of a resilient material such that when it returns to an unbiased position as illustrated in FIG. 20, the slit 284 is closed and fluid is prevented from passing therethrough.

The operation of the valve 220 will now be described in detail with reference to FIGS. 20 and 21. A user first connects the first medical implement (not shown, but which may be similar to that illustrated in FIG. 1) to the second end 232. When the first medical implement is of the type disclosed above, the free end of the tube is guided over the wall 276 between the outside of the wall and the inside of the sleeve 278. The user then engages the second medical implement 226 with the first port 231 of the valve 220. Preferably, the medical implement has a blunt cannula tip 237.

The user advances the cannula tip 237 through the seal 282 until it engages the end surface 256 of the piston 242. As the user further advances the implement, the piston 242 is pressed in the direction of the second end 232 of the housing 228, compressing the biasing member 270.

When the piston 242 is in this position (as illustrated in FIG. 21), a fluid flow path is established from the second medical implement 226 (such as through a tube from an I.V. bag) through the valve 220 to the first medical implement (and thus through the catheter to the patient). Fluid flows through the tip 237 of the cannula through the passages 257 into the passage 236. In addition, fluid fills the space 241 between the seal 282 and the piston 242. The total volume of fluid within the valve 220 when the second medical implement is engaged is an amount V1.

Most importantly, when the second medical implement 226 is disconnected from the valve 220, the valve 220 causes fluid to flow in the direction of the first medical implement through the extension passage 238. As the second medical implement 226 is disconnected, the biasing member 270 forces the piston 242 towards the first end 230 of the housing 228. As the piston 242 moves in this direction, the biasing member 270 expands. This causes the total volume or fluid space in the housing 228 to reduce. Once the piston 242 encounters the seal 184, the piston stops moving, and the fluid volume within the valve 220 is at a minimum amount V2.

Because the fluid volume in the valve 220 decreases as the second medical implement 226 is disconnected, some fluid within the housing 228 must be displaced. This fluid moves through the branch passage 238 in the direction of the patient, the total volume of fluid flowing in the "positive" direction being equal to the difference between the maximum volume V1 less the minimum volume V2.

Once the implement tip 237 is removed, the valve 220 prevents later flow of fluid from the first medical implement back through the valve 220, since the slit 284 in the seal 282 reseals, closing off the passage 236 near the first end 230 of the housing 228.

Besides providing a positive flow, the valve 220 of the present invention has other advantages. The valve 220 of the present invention has its fluid containing area between the seal 282 and the housing 228 which defines the main passage 236. This space is flushed each time fluid is injected from the top end 250 of the piston 242.

Another advantage is that the straight-through fluid flow path from the first to the second end 230,232 serves to eliminate stagnation areas.

Figure 23:
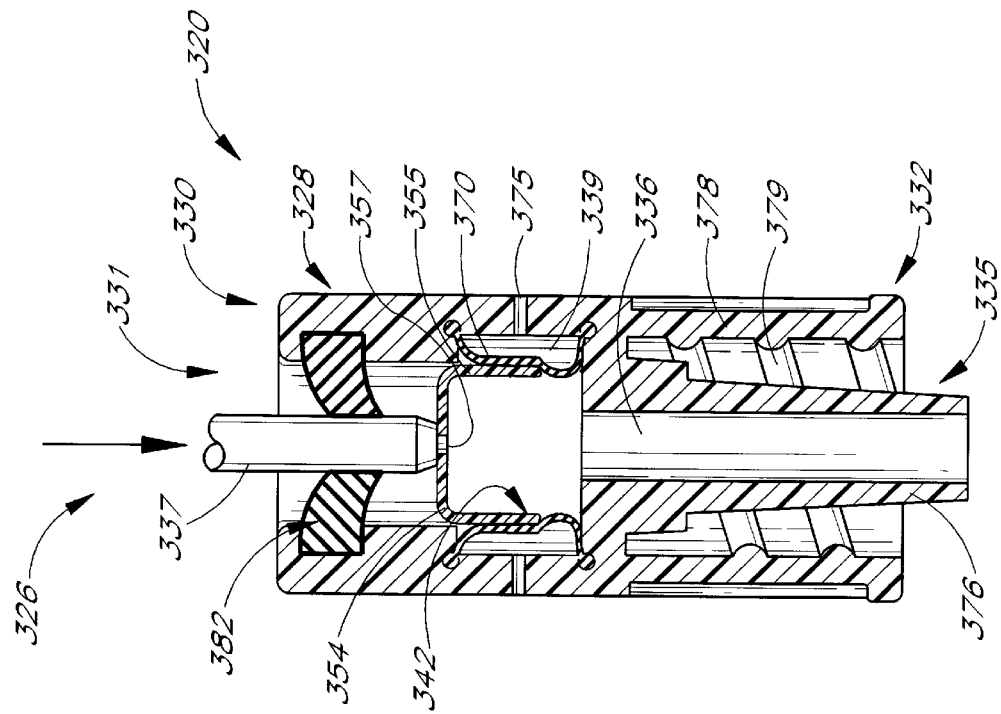
FIG. 23 is a cross-sectional side view of the valve as illustrated in FIG. 22, with the piston in a second position.
Figure 22:
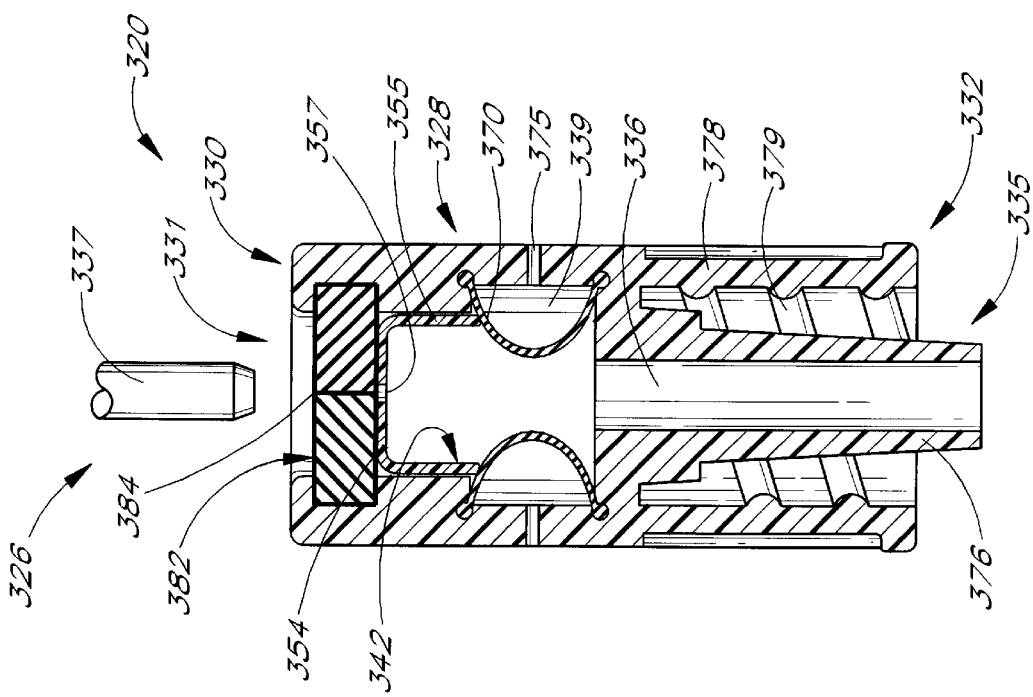
FIG. 22 is a cross-sectional side view of a valve in accordance with a fourth embodiment of the present invention, illustrating a piston of the valve in a first position.

A fourth embodiment valve 320 in accordance with the present invention is illustrated in FIGS. 22 and 23. This valve 320 includes a housing 328 which is generally cylindrical in shape, like the housing 228 of the third embodiment. The housing 328 has a first end 330 defining a first port 331 and a second end 332 defining a second port 335. A passage 336 extends through the housing 328 from end to end.

A piston 342 is movably positioned within the passage 336. The piston 342 has a generally circular head 354 with a flange or skirt 355 extending downwardly therefrom circumferentially around the outer edge of the head 354. At least one passage 357 is provided through the head 354 of the piston 342.

A biasing element 370 is positioned within the housing 328 between the piston 342 and the second end 332. As illustrated, the element 370 is a resilient member which is circular in shape having a generally "C" shaped cross-section with a closed interior side and an open exterior side.

The element 370 cooperates with an inner surface of the housing 328 to define a chamber 339 which is sealed from the passage 336. One or more vents 375 are provided through the housing wall from a point exterior thereof to the chamber 339.

In this embodiment, a sleeve 378 is surrounding a wall 376 is formed integrally with the remainder of the housing 328. The sleeve 378 has threads 379 on an inner surface thereof for use in mating engagement with threads on a medical connector.

A seal 382 is provided near the first end 330 of the housing 328. The seal 382 preferably selectively obscures or seals the passage 336 through the housing 328. The seal 382 is pre-cut to form a slit 384 which, when the seal 382 is in its unbiased position as illustrated in FIG. 22, is closed.

Use of the valve 320 of this embodiment is as follows. A user first connects a first medical implement (see FIG. 1) to the port 335 at the second end 334 of the housing 328. When the first medical implement is of the type disclosed above, a free end of the tube is guided over the wall 376 between the outside of the wall and the inside of the sleeve 378.

The user then engages the second medical implement 326 with the first port 331 of the valve 320. Preferably, the medical implement has a blunt cannula tip 337. The user advances the cannula tip 337 through the slit 384 in the seal 382 until it engages the end surface 354 of the piston 342. As the user further advances the implement, the piston 342 is pressed in the direction of the second end 332 of the housing 328, compressing the biasing element 370 radially outward. Air within the chamber 339 is forced out through the vents 375 in the wall of the housing 328.

When the piston 342 is in this position, a fluid flow path is established from the second medical implement through the valve 320 to the first medical implement. Fluid flows through the tip 337 of the cannula through the passage 357 in the first end 354 of the piston 342 into the passage 336. The total volume of fluid within the valve 320 when the second medical implement is attached and fluid fills the passage 336 with the biasing element 370 compressed is an amount V1.

Most importantly, when the second medical implement 326 is disconnected from the valve 320, the valve 320 causes fluid to flow in the direction of the first medical implement through the second port 335. As the second medical implement 326 is disconnected, the biasing element 370 forces the piston 342 towards the first end 330 of the housing 328.

At the same time, the biasing element 370 expands inwardly, causing a reduction in the total volume or fluid space in the passage 336 between the piston 342 and second end 332 of the housing 328 to reduce. Once the piston 342 moves upwardly to a point at which it encounters the seal 382, the piston stops moving, and the fluid volume within the valve 320 is at a minimum amount V2.

Because the fluid volume in the valve 320 decreases as the second medical implement 326 is disconnected, some fluid within the housing 328 must be displaced. This fluid moves through the passage 336 in the direction of the patient, the total volume of fluid flowing in the "positive" direction being equal to the difference between the maximum volume V1 less the minimum volume V2.

Once the implement tip 337 is removed, the valve 320 prevents later flow of fluid from the first medical implement therethrough, since the seal 382 closes off the passage 336 near the first end 330 of the housing 328.

Besides providing a positive flow, the valve 320 of the present invention has other advantages. Fluid stagnation is generally prevented since the fluid flows through the housing 328 in generally a straight path.

Figure 25:
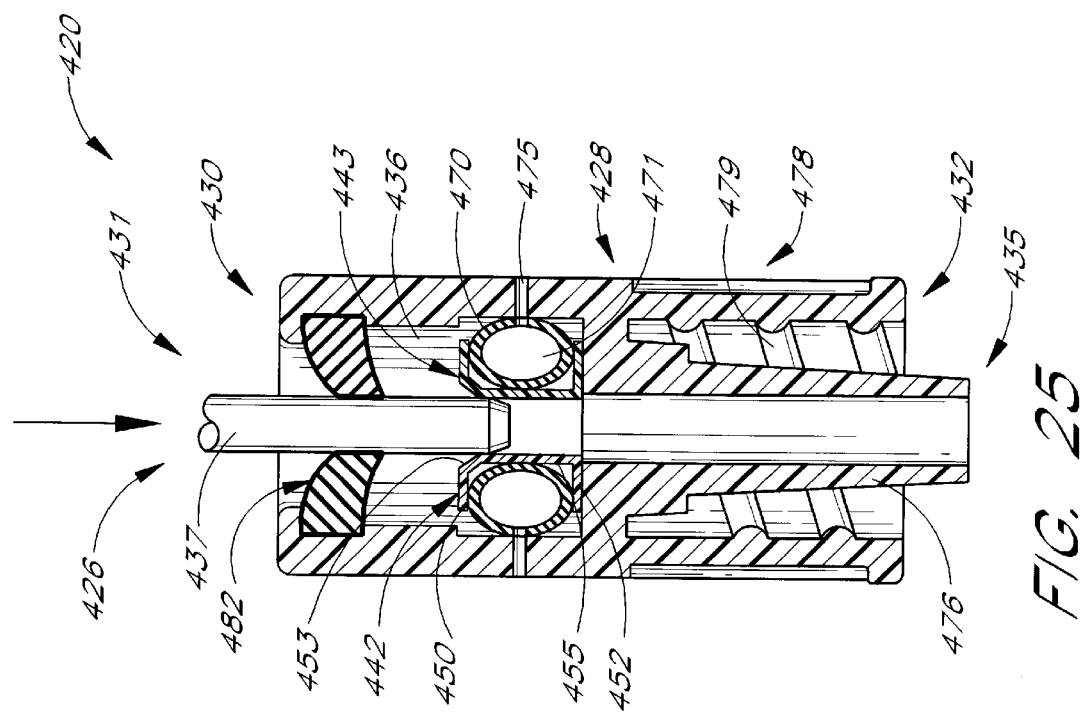
FIG. 25 is a cross-sectional side view of the valve as illustrated in FIG. 24, with the pistons in a second position.
Figure 24:
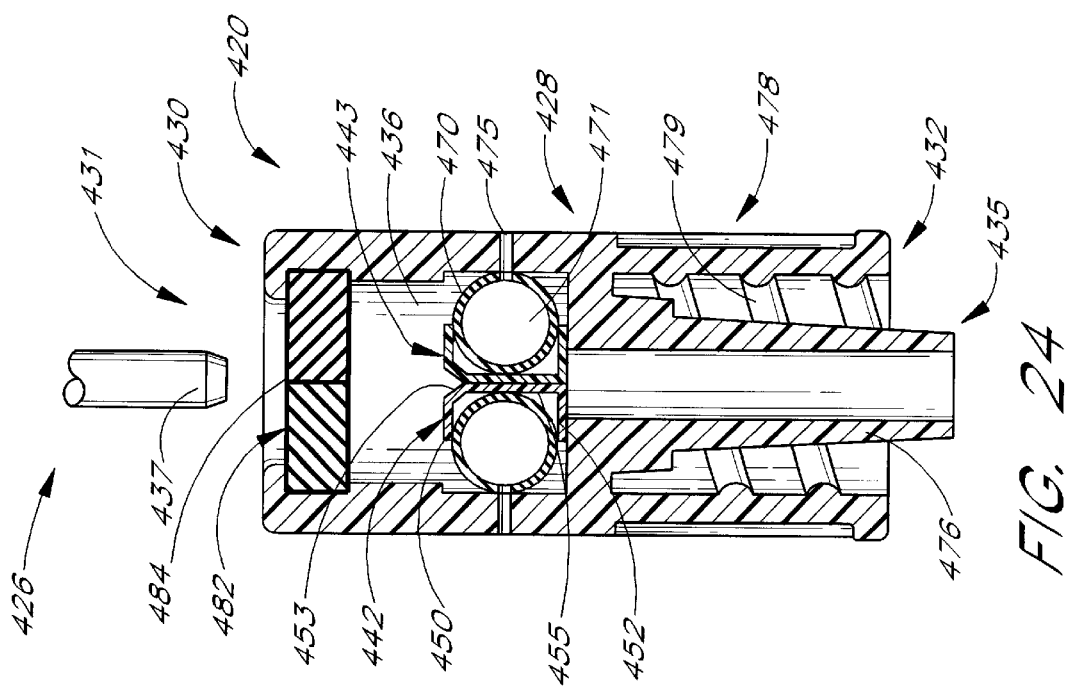
FIG. 24 is a cross-sectional side view of a valve in accordance with a fifth embodiment of the present invention, illustrating a pair of pistons of the valve in a first position.

A fifth embodiment valve 420 in accordance with the present invention is illustrated in FIGS. 24 and 25. This valve 420 includes a housing 428 which is generally identical to the housing 328 of the valve 320 described above and illustrated in FIGS. 22 and 23, having a first end 430 defining a first port 431 and a second end 432 defining a second port 435. A passage 436 extends through the housing 428 from the first to the second ends 430,432.

Again, a portion of the passage 436 near the second end 432 is defined by a wall 476. A sleeve 478 extends about the wall 476, the sleeve 478 having a number of threads 479 on an internal surface thereof.

A seal 482 which has a pre-cut slit 484 is provided near the first end 430 of the housing 428 as in the last embodiment.

In this embodiment, the biasing element 470 comprises a donut-shaped, resilient element having a hollow interior 471. The interior 471 of the element 470 is in communication with the outside of the housing 428 via one or more passages or vents 475. A connection is provided between the element 470 and the passages 475, however, so that air flowing through the passages 475 to or from the element 470 does not flow into the passage 436.

In this embodiment, a pair of pistons 442,443 move radially instead of linearly as in the previously described embodiments. Each piston 442,443 preferably includes a head 450 and a base 452 which are half-circle shaped. An upstanding wall 455 connects the head and base 450,452 of each piston 442,443 in a manner that the head and base thereof extends radially outwardly around a portion of the biasing element 470. Each piston 442,443 preferably has a tapered area 453 in the head 450 thereof, the area 453 in the pistons 442,443 cooperating to form a guide, as described in more detail below.

The pistons 442,443 are arranged to abut each other along their walls 455 in their normal position, as illustrated in FIG. 24. The pistons 442,443 are arranged to move radially outward when a medical implement is pressed between them, as illustrated in FIG. 25.

Use of the valve 420 of this embodiment is as follows. A user first connects a first medical implement (see FIG. 1) to the port 435 at the second end 434 of the housing 428. When the first medical implement is of the type disclosed above, a free end of the tube is guided over the wall 476 between the outside of the wall and the inside of the sleeve 478.

The user then engages the second medical implement 426 to the first port 431 of the valve 420. Preferably, the medical implement has a blunt cannula tip 437. The user advances the cannula tip 437 through the slit 484 in the seal 482 until it engages the head 450 of each piston 442,443. As the user further advances the implement, the pistons 442,443 are pressed radially outwardly from one another, compressing the biasing element 470. Air within the hollow interior 471 of the biasing element 470 is forced out through the vents 375 in the wall of the housing 328.

When in this position, a fluid flow path is established from the second medical implement 426 through the valve 420 to the first medical implement. Fluid flows through the tip 437 of the cannula into the passage 436. The total volume of fluid within the valve 420 when the second medical implement is attached and fluid fills the passage 436 with the biasing element 470 compressed is an amount V1.

Most importantly, when the second medical implement 426 is disconnected from the valve 420, the valve 420 causes fluid to flow in the direction of the first medical implement through the second port 435. As the second medical implement 426 is disconnected, the biasing element 470 forces the pistons 442,443 radially inwardly to that position illustrated in FIG. 24.

At the same time, the biasing element 470 expands inwardly, causing a reduction in the total volume or fluid space in the passage 436 between the piston 442 and second end 432 of the housing 428. Once the pistons 442,443 encounter one another, they stop moving and the volume within the valve 420 is at a minimum amount V2.

Because the fluid volume in the valve 420 decreases as the second medical implement 426 is disconnected, some fluid within the housing 428 must be displaced. This fluid moves through the passage 436 in the direction of the patient, the total volume of fluid flowing in the "positive" direction being equal to the difference between the maximum volume V1 less the minimum volume V2.

Once the tip 437 of the implement 426 is removed, the valve 420 prevents later flow of fluid from the first medical implement therethrough, since the seal 482 closes off the passage 436 near the first end 430 of the housing 428.

Besides providing a positive flow, the valve 420 of the present invention has other advantages. Fluid stagnation is generally prevented since the fluid flows through the housing 428 in generally a straight path.

As will be appreciated by those skilled in the art, there may be provided more than two pistons cooperating together to perform the above-described function, such as three or four "pie"-shaped pistons.

Figure 27:
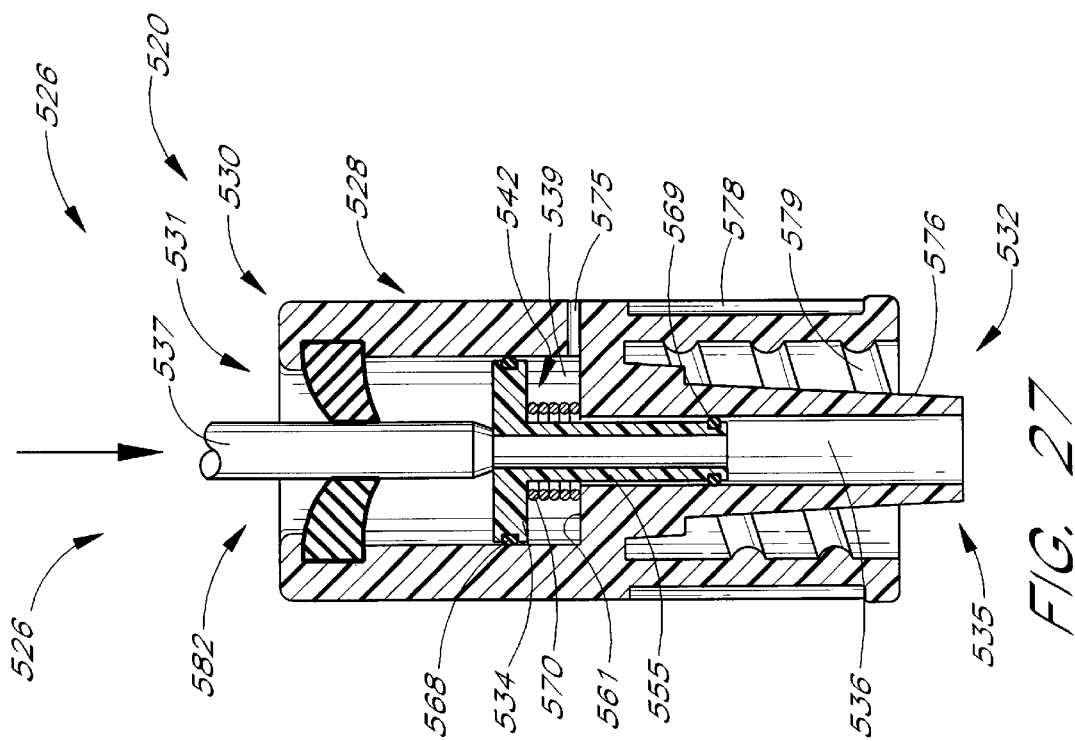
FIG. 27 is a cross-sectional side view of the valve as illustrated in FIG. 26, with the piston in a second position.
Figure 26:
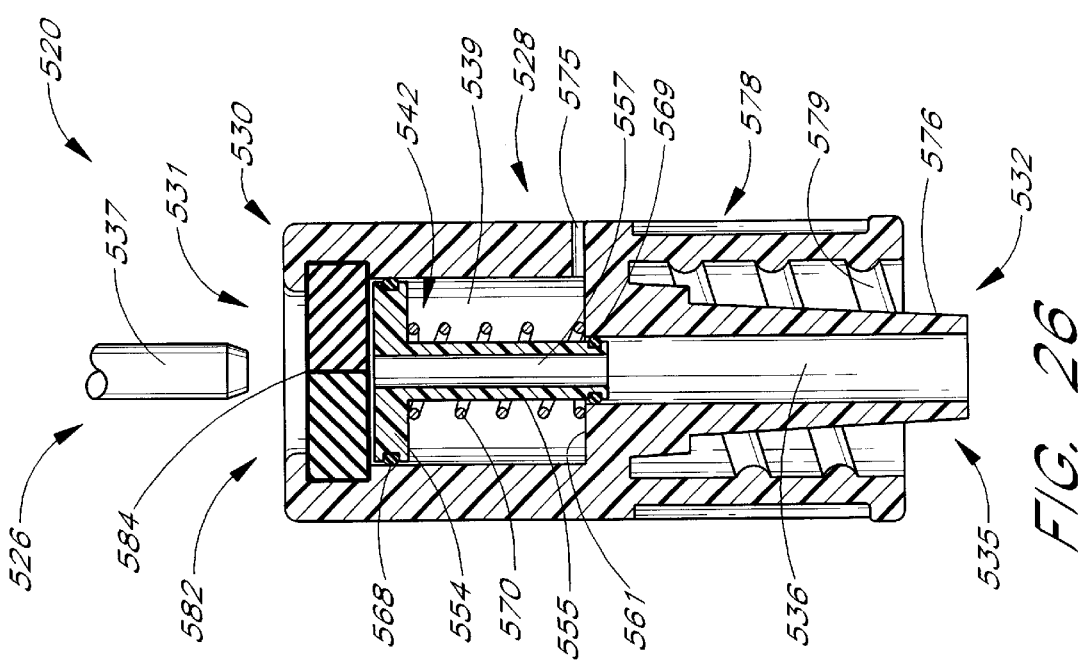
FIG. 26 is a cross-sectional side view of a valve in accordance with a sixth embodiment of the present invention, illustrating a piston of the valve in a first position.

A sixth embodiment valve 520 in accordance with the present invention is illustrated in FIGS. 26 and 27. This embodiment valve 520 is similar to the first embodiment valve 20, except that the valve 520 is arranged to have a direct flow-through arrangement similar to that illustrated in the last embodiment.

The valve 520 of this embodiment has a housing 528 which is generally cylindrical in shape. The housing 528 has a first end 530 defining a first port 531 and a second end 532 defining a second port 535. A passage 536 extends through the housing 528 from end to end.

A piston 542 is movably positioned within the passage 336. The piston 542 has a generally circular head 554 with a tubular section 555 extending centrally downwardly therefrom. A passage 557 is provided through the head 554 and tubular section 555 of the piston 542.

A spring 570 or other means for biasing is positioned within the housing 528 between the head 554 of the piston 542 and a ledge 561 formed in the housing 528 along the passage 536 between the first and second ends 530,532.

A seal 568 is provided in a groove in the circumferential surface of the head 554 of the piston 542. A similar seal 568 is provided around the tubular section 555 near its end opposite the head 554. The seals 568,569 seal off a portion of the passage 536, thereby defining a sealed, air-filled chamber 539.

One or more vents 575 are provided through the housing wall from a point exterior thereof to the chamber 539.

The sleeve 578 and wall portion 576 are integrally formed with the remainder of the housing, the wall 576 defining the passage 536 at the second end 532. The sleeve 578 has threads 579 thereon for use in mating engagement with threads on a medical connector.

A seal 582 is provided near the first end 530 of the housing 528. The seal 582 preferably obscures or seals the passage 536 through the housing 528. The seal 582 is pre-cut to form a slit 584 which, when the seal 582 is in its unbiased position as illustrated in FIG. 26, is closed.

Use of the valve 520 of this embodiment is as follows. A user first connects a first medical implement (see FIG. 1) to the port 535 at the second end 534 of the housing 528. When the first medical implement is of the type disclosed above, a free end of the tube is guided over the wall 576 between the outside of the wall and the inside of the sleeve 578.

The user then engages the second medical implement 526 to the first port 531 of the valve 520. Preferably, the medical implement has a blunt cannula tip 537. The user advances the cannula tip 537 through the slit 584 in the seal 582 until it engages the head 554 of the piston 542. As the user further advances the implement, the piston 542 is pressed in the direction of the second end 532 of the housing 528, compressing the spring 570. Air within the chamber 539 is forced out through the vents 575 in the wall of the housing 528.

When the piston 542 is in this position (as illustrated in FIG. 27), a fluid flow path is established from the second medical implement through the valve 520 to the first medical implement. Fluid flows through the tip 537 of the cannula through the passage 557 in the piston 542 into the passage 536. Fluid also fills the space between the seal 582 and the head 554 of the piston 542. The total volume of fluid within the valve 520 when the second medical implement is attached and fluid fills these areas when the spring 570 is compressed is an amount V1.

Most importantly, when the second medical implement 526 is disconnected from the valve 520, the valve 520 causes fluid to flow in the direction of the first medical implement through the second port 535. As the second medical implement 526 is disconnected, the spring 570 forces the piston 542 towards the first end 530 of the housing 528. This piston 542 movement causes a reduction in the total volume or fluid space in the passage 536 between the piston 542 and second end 532 of the housing 528. Once the piston 542 moves upwardly to a point at which it encounters the seal 582, the piston stops moving, and the fluid volume within the valve 520 is at a minimum amount V2.

Because the fluid volume in the valve 520 decreases as the second medical implement 526 is disconnected, some fluid within the housing 528 must be displaced. This fluid moves through the passage 536 in the direction of the patient, the total volume of fluid flowing in the "positive" direction being equal to the difference between the maximum volume V1 less the minimum volume V2.

Once the implement tip 537 is removed the valve 520 prevents later flow of fluid from the first medical implement therethrough, since the seal 582 closes off the passage 536 near the first end 530 of the housing 528.

Besides providing a positive flow, the valve 520 of the present invention has other advantages. Fluid stagnation is generally prevented since the fluid flows through the housing 528 in a continuous path.

Figure 29:
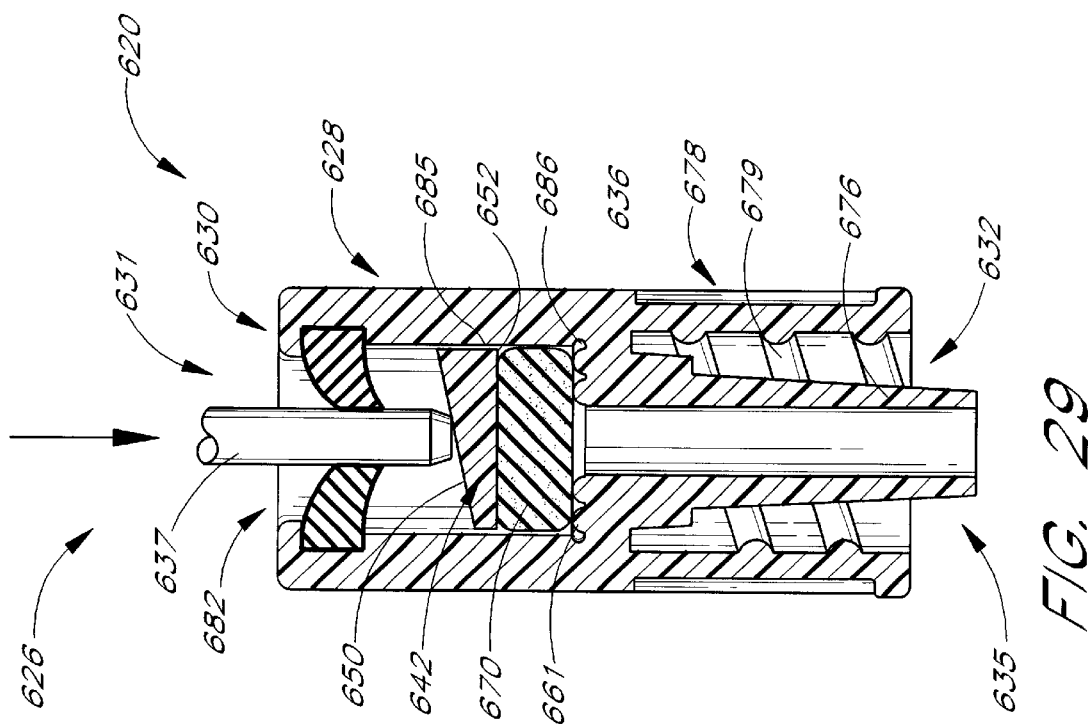
FIG. 29 is a cross-sectional side view of the valve as illustrated in FIG. 28, with the piston in a second position.
Figure 28:
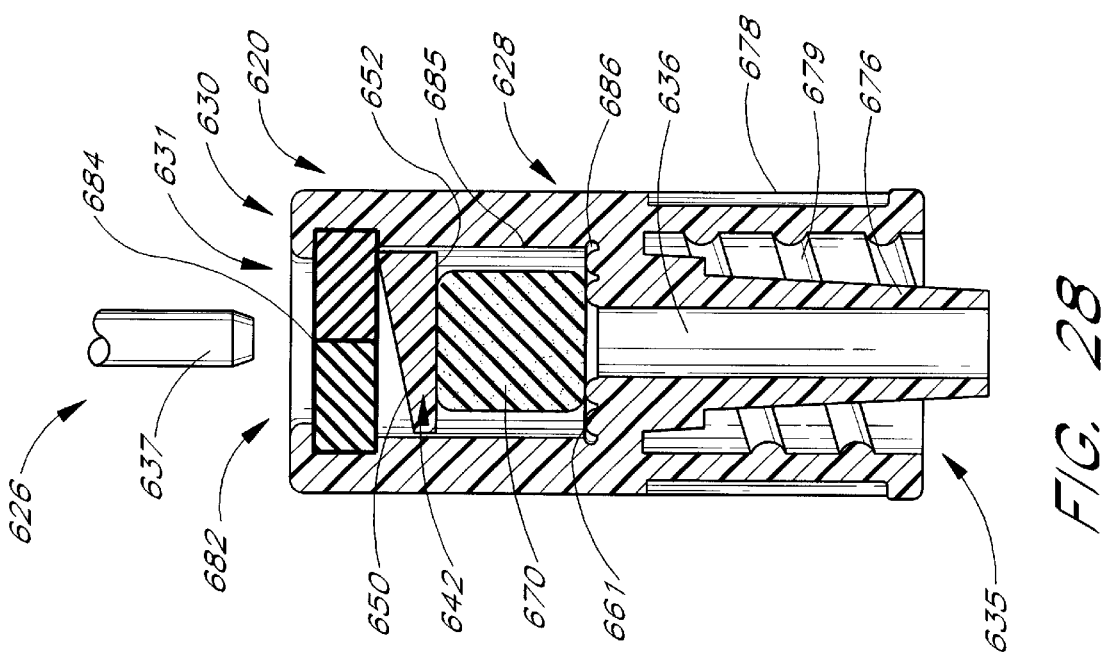
FIG. 28 is a cross-sectional side view of a valve in accordance with a seventh embodiment of the present invention, illustrating a piston of the valve in a first position.

A seventh embodiment valve 620 in accordance with the present invention is illustrated in FIGS. 28 and 29. This valve 620 includes a housing 628 which is similar to those described above with respect to valves 320, 420 and 520.

The housing 628 has a first end 630 defining a first port 631 and a second end 632 defining a second port 635. A passage 636 extends through the housing 628 from the first to the second ends 630,632.

Again, a portion of the passage 636 near the second end 632 is defined by a wall 676. A sleeve 678 extends about the wall 676, the sleeve 678 having a number of threads 679 on an internal surface thereof.

A seal 682 which has a pre-cut slit 684 is provided near the first end 630 of the housing 628 as in the last embodiment.

A piston 642 is positioned adjacent the seal 684. The piston 642 is preferably generally disc-shaped, having a circular outer shape. The piston 642 has a top or first end 650 which is slanted, and a second or bottom end 652 which is flat.

In this embodiment, a resilient element 670 comprises a generally cylindrical, resilient and non-porous material. In its resting state, the element 670 preferably has an outer diameter which is smaller than the diameter of the passage 636 in which it is positioned. The element 670 is positioned on a ledge 661 formed within the passage 636, and the bottom end 652 of the piston 642.

Grooves 685,686 are formed in the side wall of the housing 628 within the passage 636, including the portion defining the ledge 661. The grooves 685,686 are arranged to support the outside surfaces of the element 670 in a manner which permits fluid to flow between the element 670 and the housing 628, as described below.

Use of the valve 620 of this embodiment is as follows. A user first connects a first medical implement (see FIG. 1) to the port 635 at the second end 634 of the housing 628. When the first medical implement is of the type disclosed above, a free end of the tube is guided over the wall 676 between the outside of the wall and the inside of the sleeve 678.

The user then engages the second medical implement 626 to the first port 631 of the valve 620. Preferably, the medical implement has a blunt cannula tip 637. The user advances the cannula tip 637 through the slit 684 in the seal 682 until it engages the top 650 of the piston 642. As the user further advances the implement, the piston 642 is pressed downwardly compressing the element 670.

When in this position, a fluid flow path is established from the second medical implement 626 through the valve 620 to the first medical implement. Fluid flows through the tip 637 of the cannula through the passage 636. Fluid is allowed to flow past the element 670 through the grooves 685, 686. The total volume of fluid within the valve 620 when the second medical implement is attached and fluid fills the passage 636 and that space between the top 650 of the piston 642 and the bottom of the seal 682 when the piston 642 is depressed is an amount V1.

Most importantly, when the second medical implement 626 is disconnected from the valve 620, the valve 620 causes fluid to flow in the direction of the first medical implement through the second port 635. As the second medical implement 626 is disconnected, the element 670 expands, forcing the piston 642 upwardly to that position illustrated in FIG. 28.

At the same time, a reduction in the total volume or fluid space in the passage 636 between the piston 642 and seal 682 occurs. Once the piston 642 moves upwardly to a point at which it encounters the seal 682, the piston stops moving, and the fluid volume within the valve 620 is at a minimum amount V2.

Because the fluid volume in the valve 620 decreases as the second medical implement 626 is disconnected, some fluid within the housing 628 must be displaced. This fluid moves through the passage 636 in the direction of the patient, the total volume of fluid flowing in the "positive" direction being equal to the difference between the maximum volume V1 less the minimum volume V2.

Once the tip 637 of the implement 626 is removed, the valve 620 prevents later flow of fluid from the first medical implement therethrough, since the seal 682 closes off the passage 636 near the first end 630 of the housing 628.

Besides providing a positive flow, the valve 620 of the present invention has other advantages. Fluid stagnation is generally prevented since the fluid flows through the housing 628 in generally a straight path.

Figure 31:
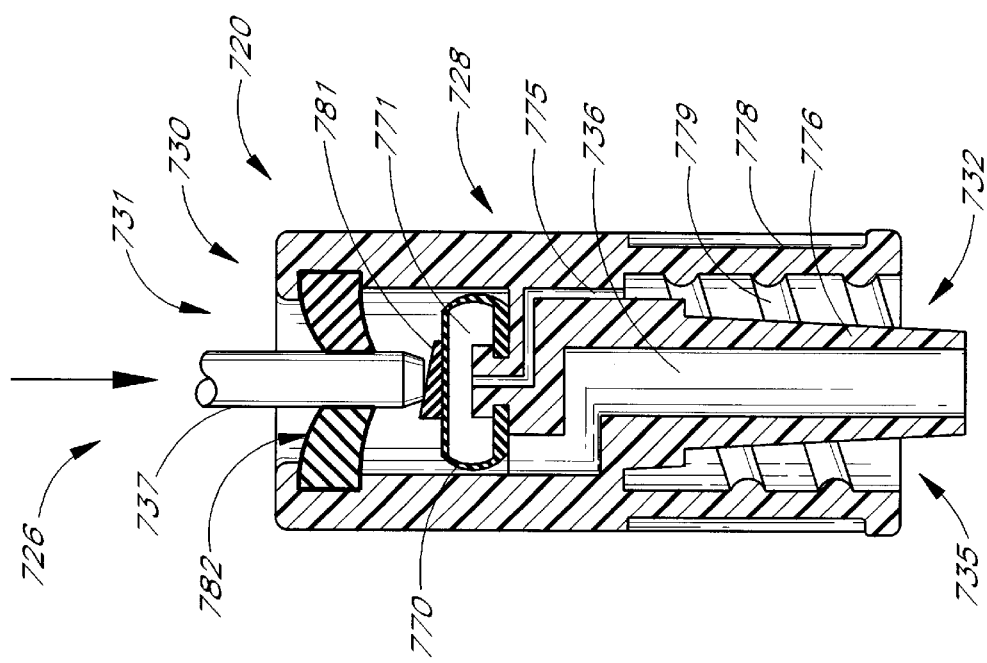
FIG. 31 is a cross-sectional side view of the valve as illustrated in FIG. 30, with the element in a second position.
Figure 30:
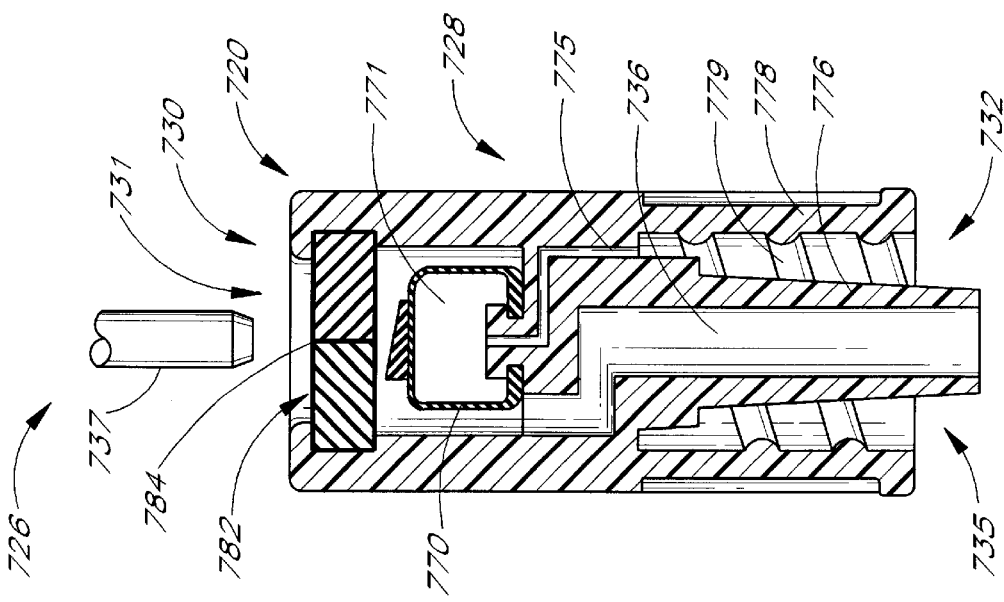
FIG. 30 is a cross-sectional side view of a valve in accordance with a eighth embodiment of the present invention, illustrating a resilient element of the valve in a first position.

An eighth embodiment valve 720 in accordance with the present invention is illustrated in FIGS. 30 and 31. This valve 720 includes a housing 728 which is similar to those described above with respect to valves 220, 320 etc.

The housing 728 has a first end 730 defining a first port 731 and a second end 732 defining a second port 735. A passage 736 extends through the housing 728 from the first to the second ends 730,732.

Again, a portion of the passage 736 near the second end 732 is defined by a wall 776. A sleeve 778 extends about the wall 776, the sleeve 778 having a number of threads 779 on an internal surface thereof.

A seal 782 which has a pre-cut slit 784 is provided near the first end 730 of the housing 728 as in the last embodiment.

In this embodiment, a resilient element 770 comprises a generally cylindrical, resilient and hollow member. In its resting state, the element 770 preferably has an outer diameter which is smaller than the diameter of the passage 736 in which it is positioned. The element 770 defines a interior space 771 which is sealed from the passage 736. The element 770 is positioned on a ledge 761 formed within the housing 728.

A sloped canula-engaging surface 781 is defined at the top of the element 770.

A vent 775 extends through the housing 628 from the interior space 771 within the element 770 to a point exterior of the housing 628. In the embodiment illustrated, the vent 775 terminates in the space between the wall 776 and the sleeve 778.

Use of the valve 720 of this embodiment is as follows. A user first connects a first medical implement (see FIG. 1) to the port 735 at the second end 734 of the housing 728. When the first medical implement is of the type disclosed above, a free end of the tube is guided over the wall 776 between the outside of the wall and the inside of the sleeve 778.

The user then engages the second medical implement 726 to the first port 731 of the valve 720. Preferably, the medical implement has a blunt cannula tip 737. The user advances the cannula tip 737 through the slit 784 in the seal 782 until it engages the sloped surface 781 at the top of the element 770. As the user further advances the implement, the element 770 is compressed downwardly and outwardly, reducing the volume of the space 771, but increasing the fluid space within the valve 720.

When in this position, a fluid flow path is established from the second medical implement 726 through the valve 720 to the first medical implement. Fluid flows through the tip 737 of the cannula along the sloped surface 781 (whereby the tip of the canula is not obstructed) and through the passage 736. The total volume of fluid within the valve 720 when the second medical implement is attached and fluid fills the passage 736 and that space between the top of the element 770 and the bottom of the seal 782 is an amount V1.

Most importantly, when the second medical implement 726 is disconnected from the valve 720, the valve 720 causes fluid to flow in the direction of the first medical implement through the second port 735. As the second medical implement 726 is disconnected, the element 770 moves upwardly to that position illustrated in FIG. 30.

At the same time, a reduction in the total volume or fluid space in the passage 736 between element 770 and the seal 782 occurs, until the fluid volume within the valve 720 is at a minimum amount V2.

Because the fluid volume in the valve 720 decreases as the second medical implement 726 is disconnected, some fluid within the housing 728 must be displaced. This fluid moves through the passage 736 in the direction of the patient, the total volume of fluid flowing in the "positive" direction being equal to the difference between the maximum volume V1 less the minimum volume V2.

Once the tip 737 of the implement 726 is removed, the valve 720 prevents later flow of fluid from the first medical implement therethrough, since the seal 782 closes off the passage 736 near the first end 730 of the housing 728.

Besides providing a positive flow, the valve 720 of the present invention has other advantages. Fluid stagnation is generally prevented since the fluid flows through the housing 728 in generally a straight path.

Figure 32:
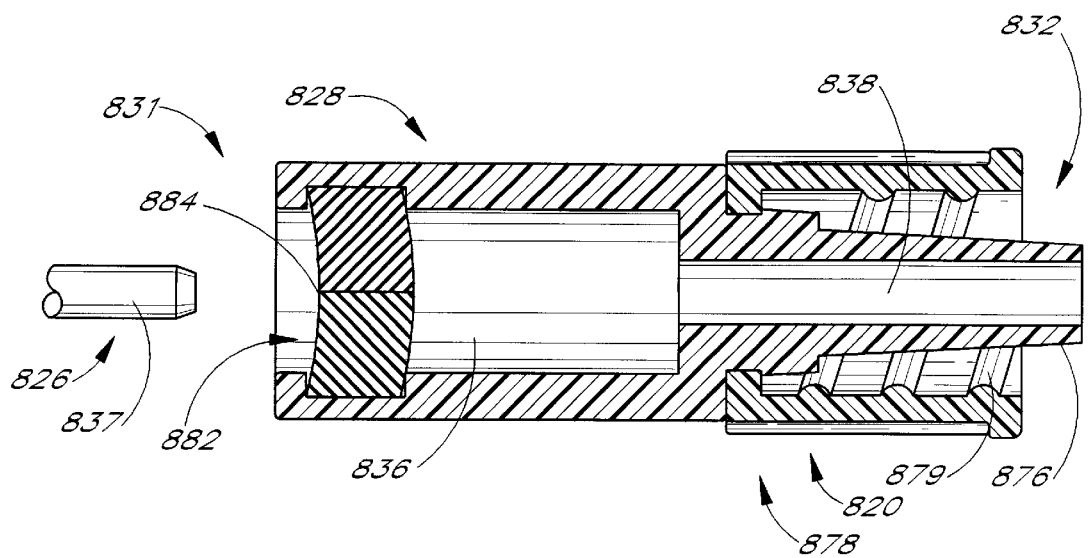
FIG. 32 is a cross-sectional side view of a valve in accordance with a ninth embodiment of the present invention, illustrating a seal of the valve in a first position.
Figure 33:
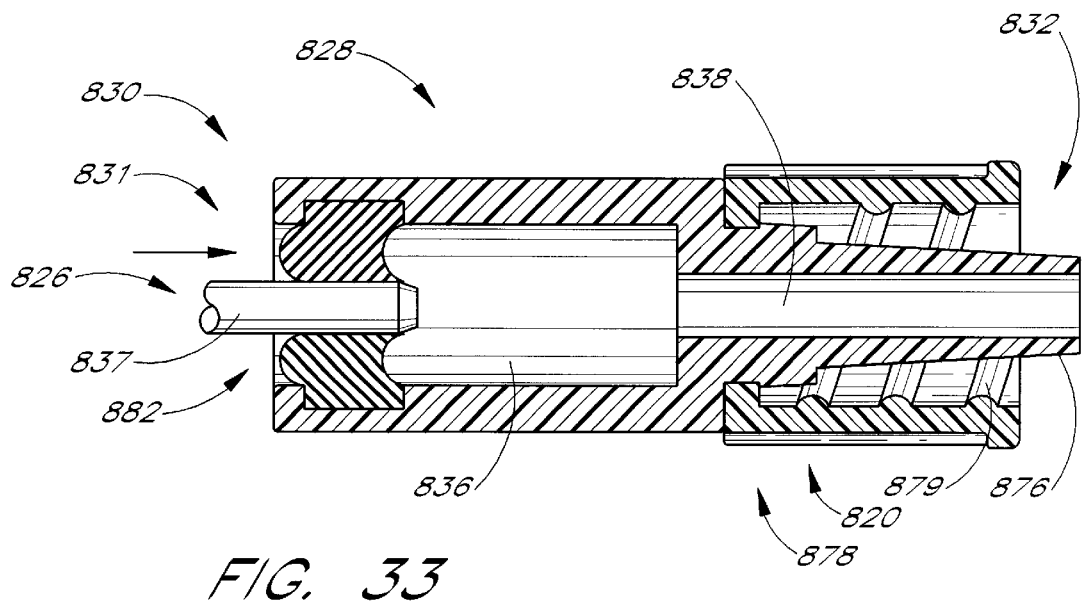
FIG. 33 is a cross-sectional side view of the valve as illustrated in FIG. 32, with the seal in a second position.

A ninth embodiment valve 820 in accordance with the present invention is illustrated in FIGS. 32 and 33. As illustrated, this valve 820 includes a housing 828 which is somewhat similar to the housings of the valves 220, 320 etc. described above.

As illustrated, the housing 828 has a body having a first end 830 defining a first port 831 and an opposing second end 832. A main passage 836 extends from the first end 830 towards the second end 832 of the housing. The main passage 836 is defined by an inner surface of a wall of the housing 828. The main passage 836 is cylindrical in shape.

An extension passage 838 extends from the main passage 836 to the second end 832. The extension passage 838 is preferably defined by a wall 876 and is generally cylindrical in shape, although smaller in diameter than the main passage 836.

A resilient, seal 882 is provided near the first end 830 of the housing 828. The seal 882 has a generally circular or peripheral outer shape for fitting within the passage 836, and preferably includes a pre-formed slit 884 through which the tip of a medical implement may pass. The seal 882 is preferably constructed of a resilient material such that it naturally returns to the position as illustrated in FIG. 32, where the slit 884 is closed and fluid is prevented from passing therethrough.

More importantly, however, the seal 882 is arranged so that when an implement is pressed through the slit 884, at least a portion of the seal 882 moves in the direction of the first end 830 of the housing 828 whereby the fluid space or volume inside the housing 828 increases. At the same time, the seal 882 is arranged so that when the implement is retracted, the seal 882 moves in the direction of the second end 832 of the housing 828, reducing the fluid space or volume therein.

A sleeve 878 is positioned about the wall 876 at the second end 832 of the housing 828. The sleeve 878 preferably has threads 879 on an inner surface thereof.

The operation of the valve 820 will now be described in detail with reference to FIGS. 32 and 33. A user first connects the first medical implement (not shown, but which may be similar to that illustrated in FIG. 1) to the branch port 835 at the third end 834. When the first medical implement is of the type disclosed above, the free end of the tube is guided over the wall 876 between the outside of the wall and the inside of the sleeve 878.

The user then engages the second medical implement 826 to the first port 831 of the valve 820. Preferably, the medical implement has a blunt cannula tip 837. The user advances the cannula tip 837 through the slit 884 in the seal 882. At this time, the seal 882 moves into the position as illustrated in FIG. 33.

When in this position, a fluid flow path is established from the second medical implement 826 (such as through a tube from an I.V. bag) through the valve 820 to the first medical implement (and thus through the catheter to the patient). Fluid flows through the tip 837 of the cannula through the main passage 836 and extension passage 838. The total volume of fluid within the valve 820 when the second medical implement is attached is an amount V1.

Most importantly, when the second medical implement 826 is disconnected from the valve 820, the valve 820 causes fluid to flow in the direction of the first medical implement through the extension passage 838. As the second medical implement 826 is disconnected, the seal 882 moves back to its position as illustrated in FIG. 32. This causes the total volume or fluid space in the housing 828 to reduce to a minimum amount V2.

Because the fluid volume in the valve 820 decreases as the second medical implement 826 is disconnected, some fluid within the housing 828 must be displaced. This fluid moves through the branch passage 838 in the direction of the patient, the total volume of fluid flowing in the "positive" direction being equal to the difference between the maximum volume V1 less the minimum volume V2.

Once the implement tip 837 is removed, the valve 820 prevents later flow of fluid from the first medical implement therethrough, since the slit 884 in the seal 882 reseals, closing off the passage 836 near the first end 830 of the housing 828.

Besides providing a positive flow, the valve 820 of the present invention has other advantages. The valve 820 of the present invention has its fluid containing area between the seal 882 and the housing 828 which defines the main passage 836. This space is flushed each time fluid is injected through the implement 826.

Figure 34:
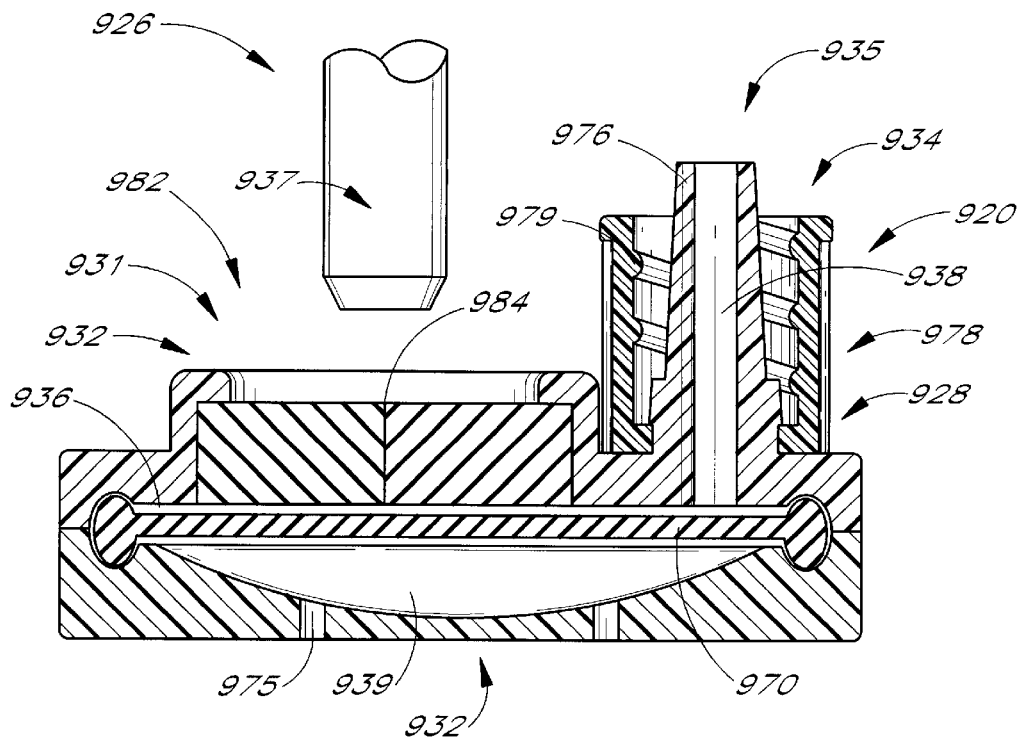
FIG. 34 is a cross-sectional side view of a valve in accordance with a tenth embodiment of the present invention, illustrating a diaphragm of the valve in a first position.
Figure 35:
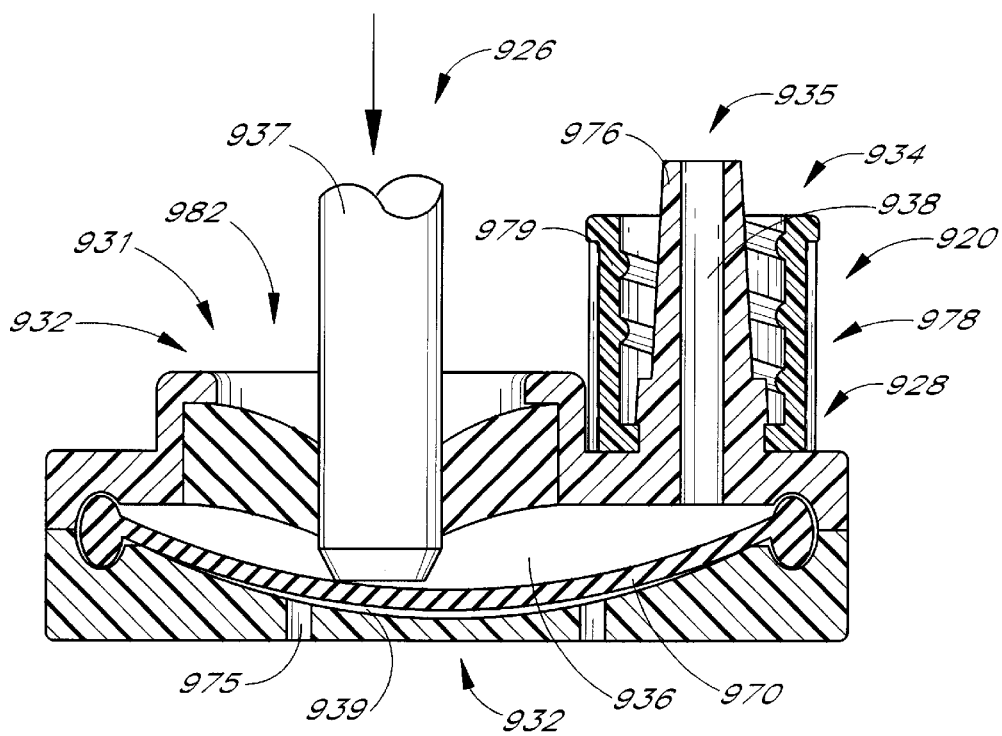
FIG. 35 is a cross-sectional side view of the valve as illustrated in FIG. 34, with the diaphragm in a second position.

A tenth embodiment valve 920 in accordance with the present invention is illustrated in FIGS. 34 and 35. As illustrated, the housing 928 has a body having a first end 930 defining a first port 931 and an opposing closed second end 932. A branch 933 extends to a third end 934 defining a branch port 935.

An opening in the housing 928 at its first end leads to a chamber 936 or passage on one side of a diaphragm member 970 to a branch passage 938. The branch passage 938 extends from the chamber 936 in the direction opposite the second end 930 of the housing 928. The branch passage 938 is preferably defined by a wall 976. The branch passage 938 is generally cylindrical in shape.

A resilient, pre-slit seal 982 is provided near the first end 930 of the housing 928. The seal 982 is generally circular for fitting within the opening in the first end 930 of the housing 928. The seal 982 preferably includes a pre-formed slit 984 through which the tip of a medical implement may pass. The seal 982 is preferably constructed of a resilient material such that it naturally returns to the position illustrated in FIG. 34, where the slit 984 is closed and fluid is prevented from passing therethrough.

The diaphragm 970 is positioned within a hollow space within the housing 928 between the first and second ends 920,932. The diaphragm 970 generally divides this space into the first chamber or cavity 936 and a second chamber 939. The diaphragm 970 is biased in an upward direction, i.e., in the direction of the first end 930 of the housing 929.

At least one vent 975 extends through the wall of the housing 928 at its second end 932 to the second chamber 939, permitting air to flow in and out of the chamber.

As with the first embodiment, a sleeve 978 is positioned about the branch 933 of the housing 928. The sleeve 978 preferably has threads 979 on an inner surface thereof.

The operation of the valve 920 will now be described in detail with reference to FIGS. 34 and 35. A user first connects the first medical implement (not shown, but which may be similar to that illustrated in FIG. 1) to the branch port 935 at the third end 934. When the first medical implement is of the type disclosed above, the free end of the tube is guided over the wall 976 between the outside of the wall and the inside of the sleeve 978.

The user then engages the second medical implement 926 to the first port 931 of the valve 920. Preferably, the medical implement has a blunt cannula tip 937. The user advances the cannula tip 937 through the slit 984 in the seal 982 and presses upon the diaphragm 970. At this time, the diaphragm 970 moves into the position as illustrated in FIG. 35.

When in this position (as illustrated in FIG. 35), a fluid flow path is established from the second medical implement 926 (such as through a tube from an I.V. bag) through the valve 920 to the first medical implement (and thus through the catheter to the patient). Fluid flows through the tip 937 of the cannula into the chamber 936, then through the branch passage 938. The total volume of fluid within the valve 920 when the second medical implement is attached is an amount V1.

Most importantly, when the second medical implement 926 is disconnected from the valve 920, the valve 920 causes fluid to flow in the direction of the first medical implement through the branch passage 938. As the second medical implement 926 is disconnected, the diaphragm 970 moves upwardly back to its position as illustrated in FIG. 34. This causes the total volume or fluid space in the housing 928 to reduce to a minimum amount V2.

Because the fluid volume in the valve 920 decreases as the second medical implement 926 is disconnected, some fluid within the housing 928 must be displaced. This fluid moves through the branch passage 938 in the direction of the patient, the total volume of fluid flowing in the "positive" direction being equal to the difference between the maximum volume V1 less the minimum volume V2.

Further, once the implement tip 937 is removed, the valve 920 prevents later flow of fluid from the first medical implement therethrough, since the slit 984 in the seal 982 reseals, closing off the passage 936 near the first end 930 of the housing 928.

Besides providing a positive flow, the valve 920 of the present invention has other advantages. The valve 920 of the present invention has its fluid containing area between the seal 982 and the housing 928 which defines the chamber 936. This space is flushed each time fluid is injected through the implement 926.

An eleventh embodiment valve 1020 in accordance with the present invention is illustrated in FIGS. 36–48. This valve 1020 is similar in many respects to the valve of the first embodiment.

Figure 36:
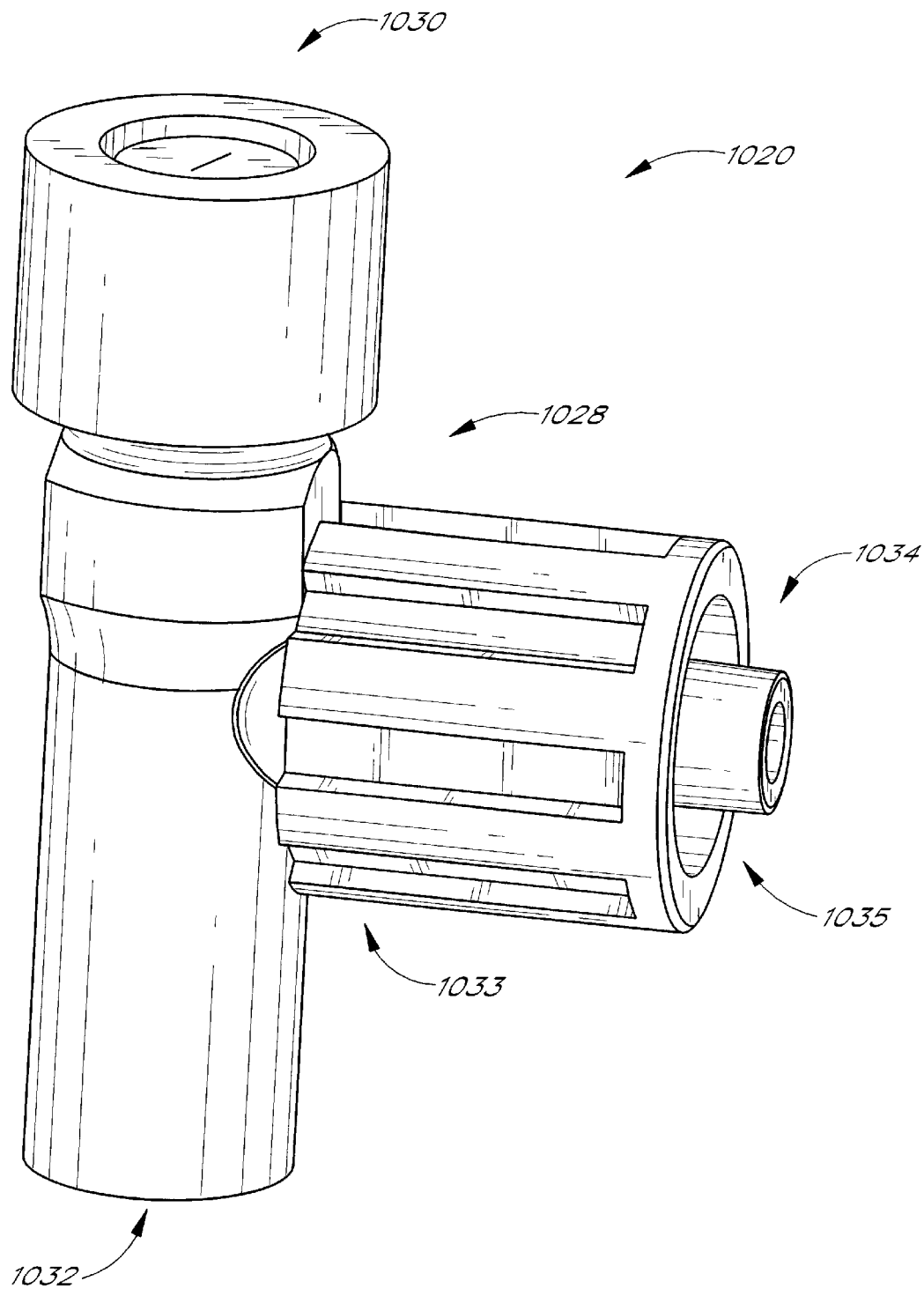
FIG. 36 is a perspective view of a valve in accordance with an eleventh embodiment of the present invention.
Figure 40:
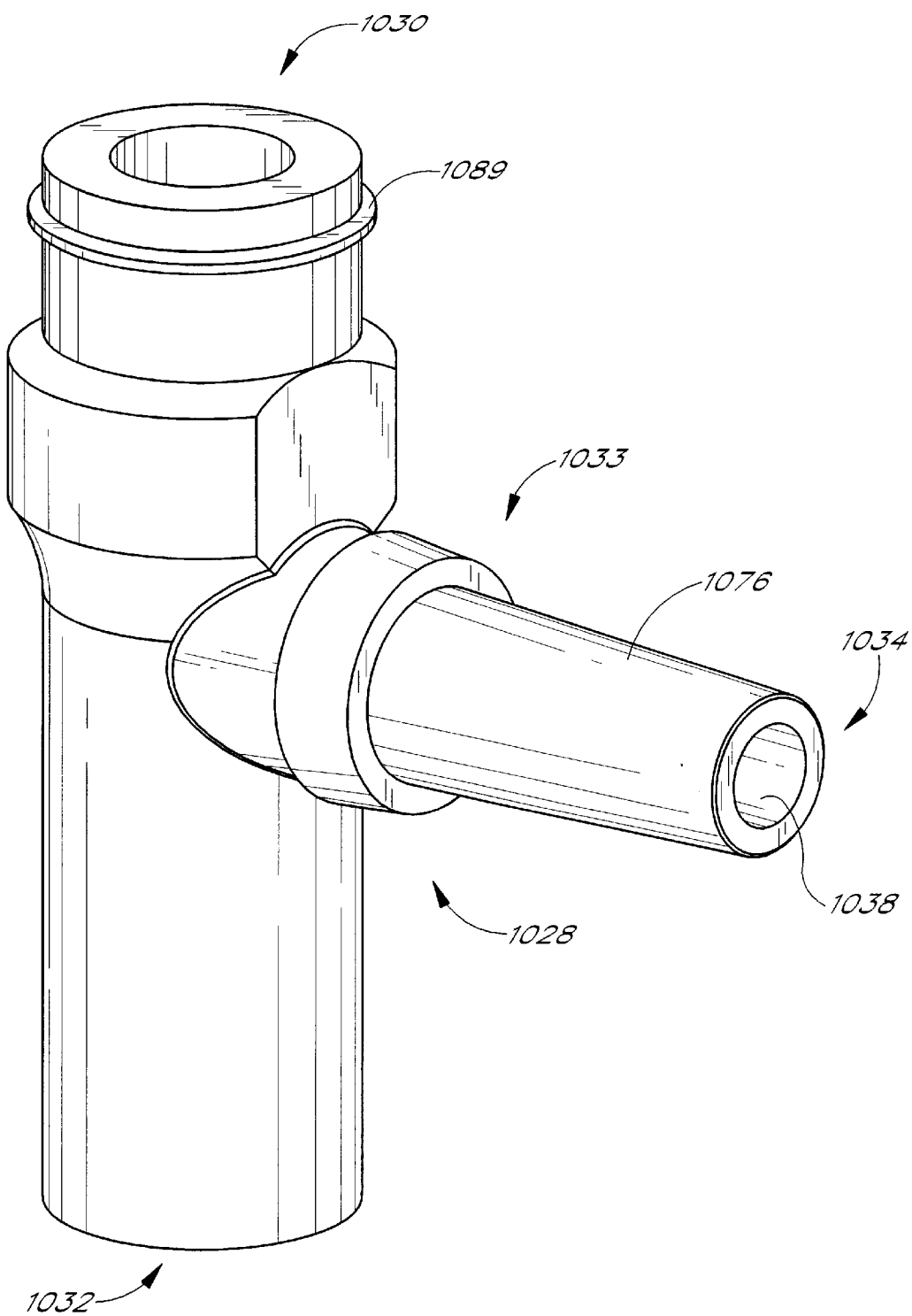
FIG. 40 is a perspective view of a housing of the valve illustrated in FIG. 36.
Figure 41:
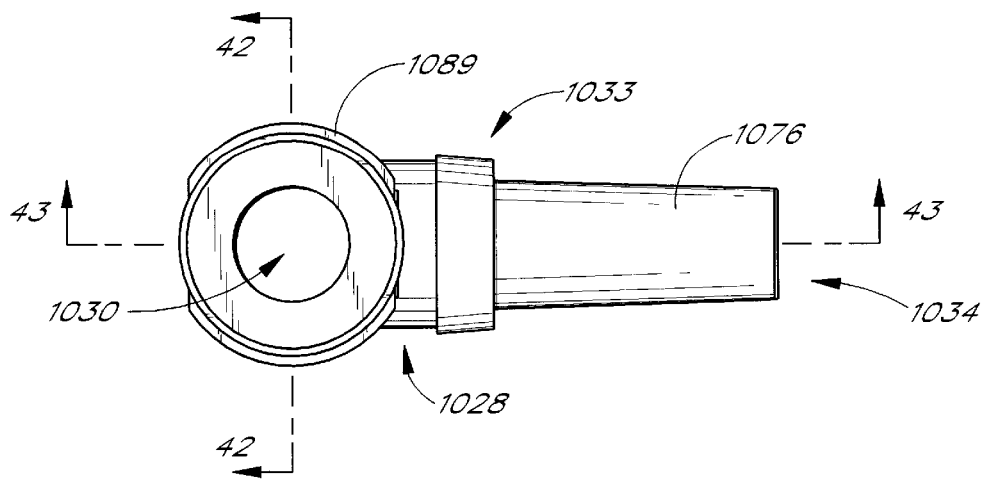
FIG. 41 is a top view of the housing illustrated in FIG. 40.
Figures 42, 43:
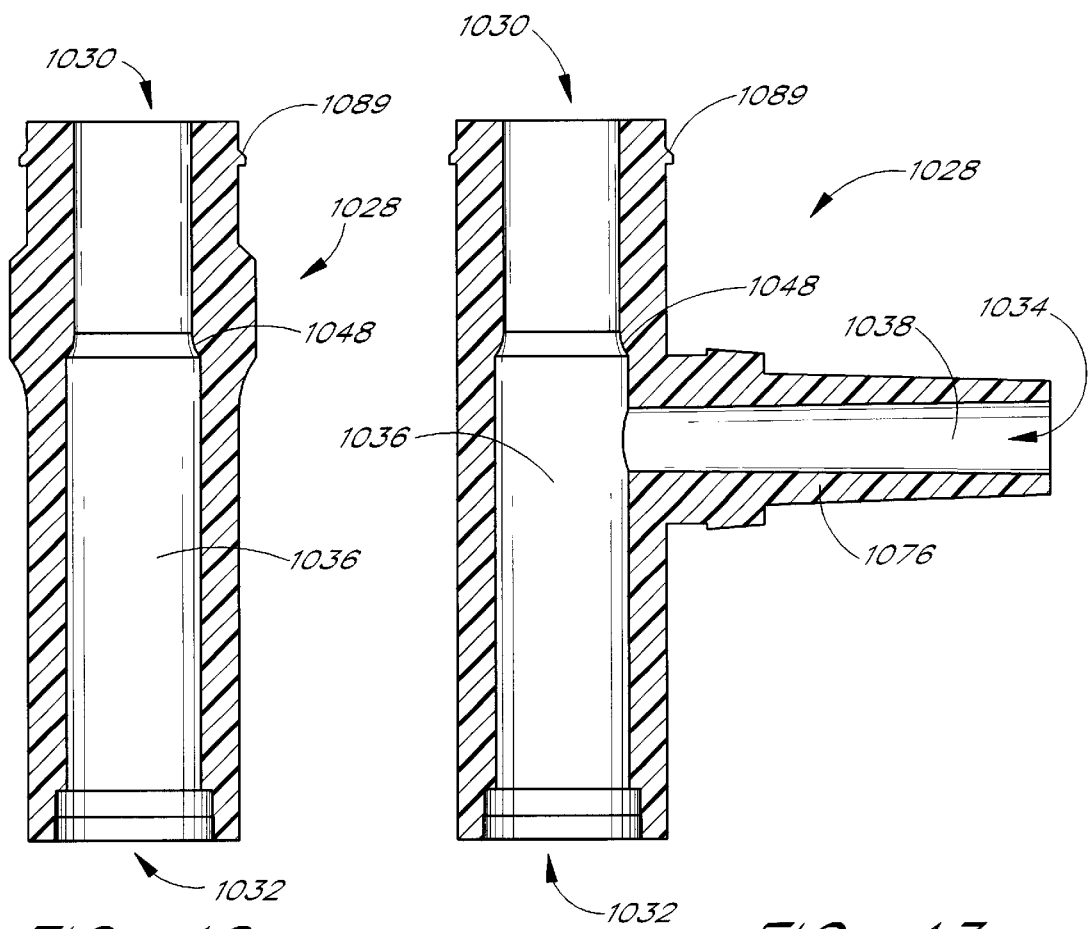
FIG. 42 is a cross-sectional view of the housing illustrated in FIG. 41 taken along line 42—42 therein.
FIG. 43 is a cross-sectional view of the housing illustrated in FIG. 41 taken along line 43—43 therein.
Figure 44:
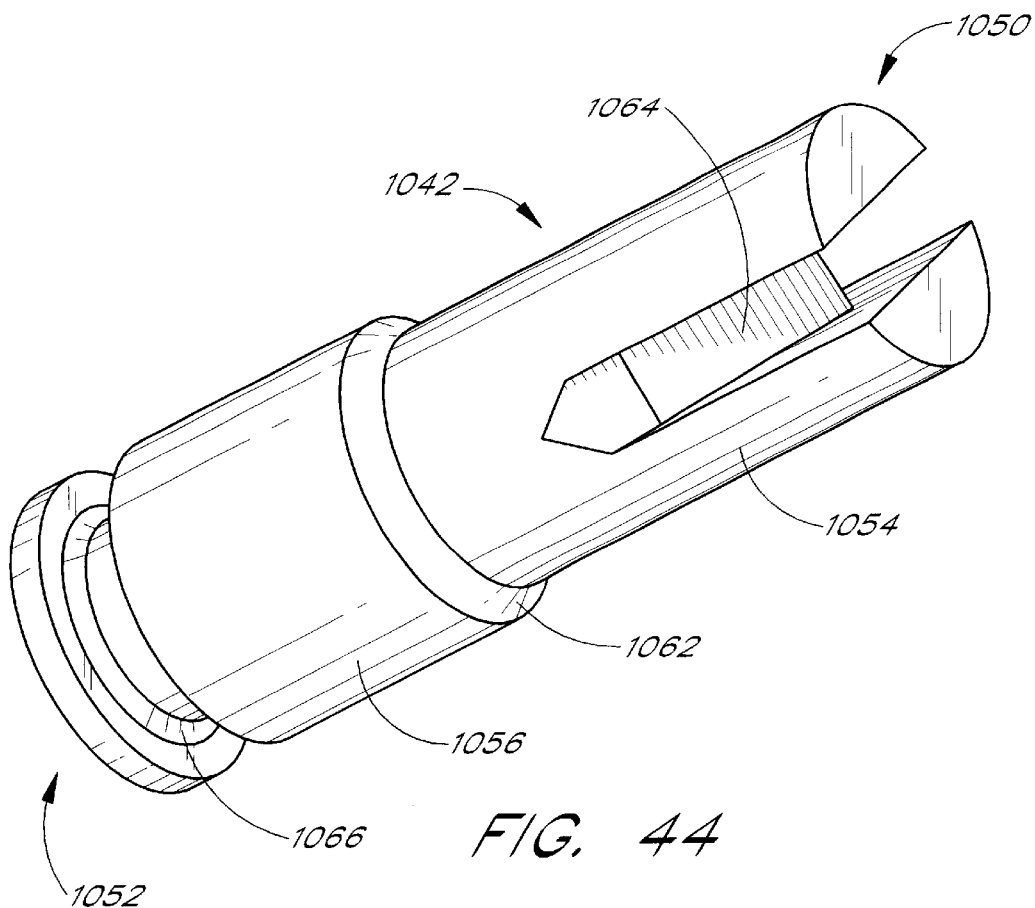
FIG. 44 is a perspective view of the piston of the valve.
Figure 45:
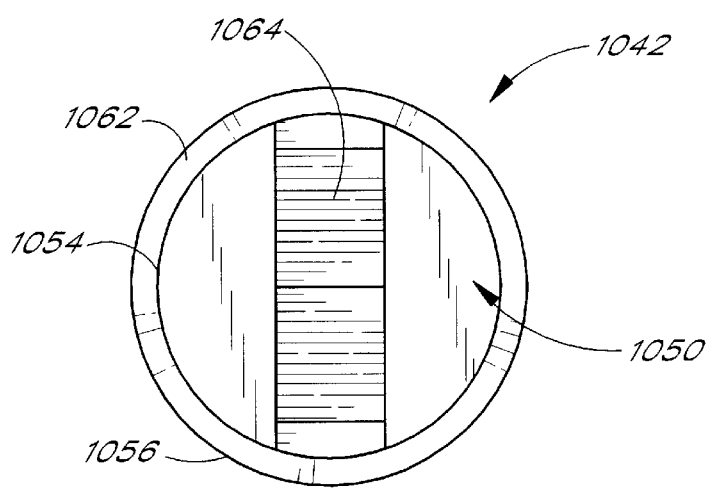
FIG. 45 is a top view of the piston illustrated in FIG. 44.
Figure 46:
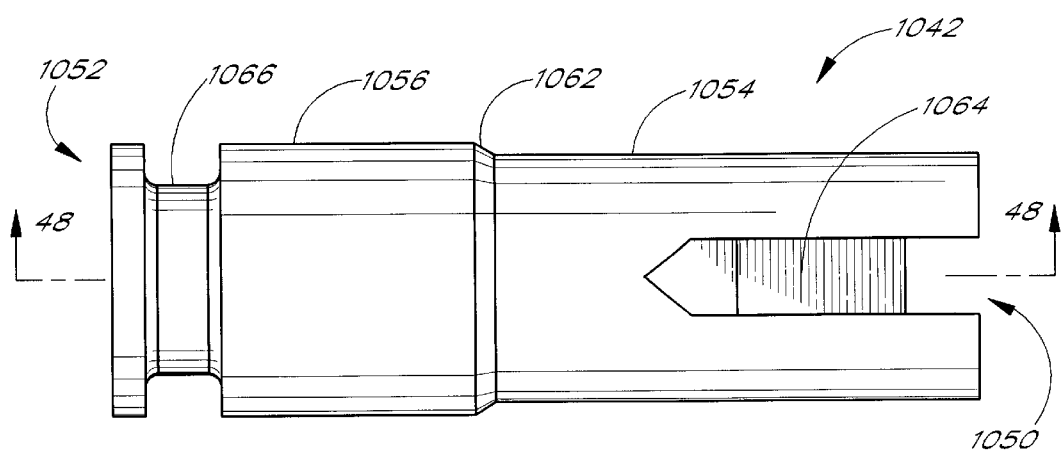
FIG. 46 is a side view of the piston illustrated in FIG. 44.
Figure 47:
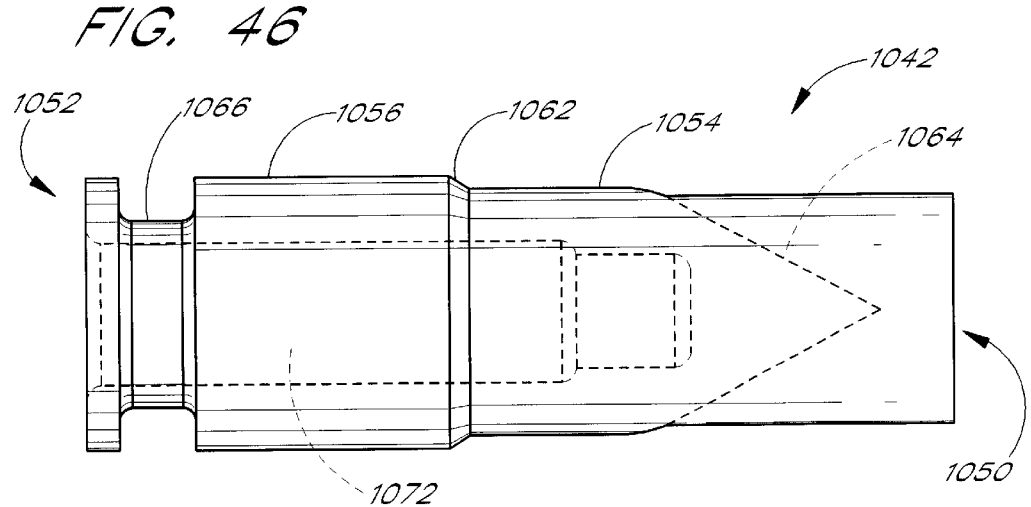
FIG. 47 is a second side view of the piston illustrated in FIG. 44.
Figure 48:
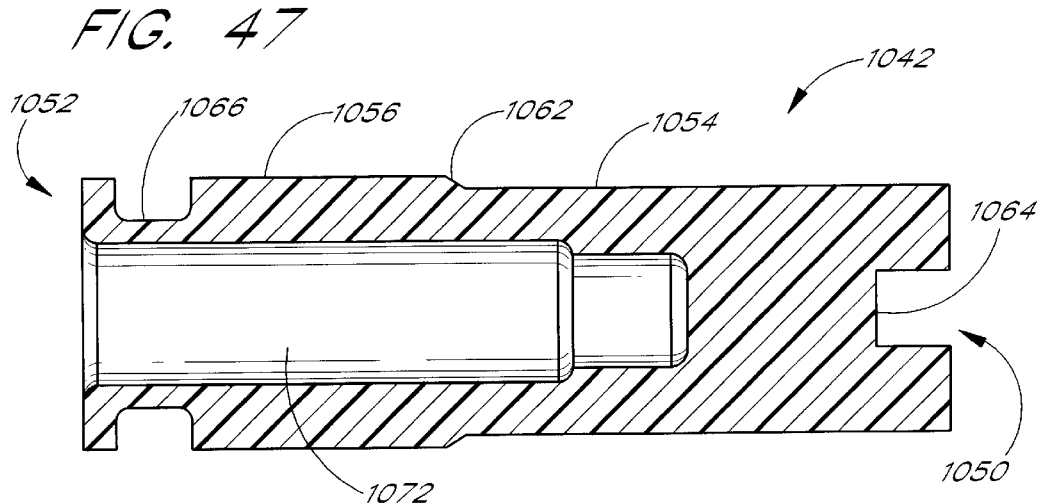
FIG. 48 is a cross-sectional view of the piston illustrated in FIG. 46 taken along line 48—48 therein.

Referring to FIG. 36, the valve 1020 includes a housing 1028 which is "T"-shaped, having a main portion with a first end 1030 and an opposing, closed second end 1032. A branch 1033 extends outwardly from the main portion generally perpendicular thereto to a third end 1034 defining a branch port 1035.

As illustrated in FIGS. 38 and 39, a main passage 1036 extends from the first end 1030 to the closed second end 1032 inside of the housing 1028. In addition, a branch passage 1038 extends from the main passage 1036 through the branch port to the third end 1034.

The main passage 1036 has two diameters. A first small diameter portion of the passage 1036 extends from the first end 1030 to near the branch passage 1038. The diameter of the main passage 1036 then increases to a larger diameter section extending to the second end 1032. A ledge 1048 is formed at the intersection of these two portions of the main passage 1036.

A piston 1042 is slidably positioned within the main passage 1036. Referring to FIGS. 44–48, the piston 1042 is generally cylindrical, having a maximum outer diameter which is slightly less than the maximum diameter of the passage 1036. The piston 1042 has a first end 1050 and a second end 1052 and a length from end to end which is less than the distance from the first end 1030 to the second end 1032 of the housing 1028.

The piston 1042 has a first body portion 1054 extending from the first end 1050 to a second body portion 1056. The outer diameter of the second body portion 1056 is larger than that of the first body portion 1054, with a shoulder 1062 defining the intersection of these two portions. This shoulder 1062 is arranged to engage the ledge 1048 in the housing 1028 in a manner described below.

A groove 1066 is formed in the piston 1042 near its second end 1052. Preferably, a seal 1068 (see FIGS. 38 and 39) is positioned in this groove 1066. The seal 1068 preferably comprises an "O"-ring.

A "V"-shaped notch or cutout 1064 is defined in the first body portion 1056 of the piston 1042. This notch 1064 extends from the first end 1050 towards the second end 1052.

In the preferred embodiment, the piston 1042 is hollow, having a recessed area therein. As illustrated, this area comprises a bore 1072 extending into the piston 1042 from the second end 1052. As illustrated, the bore 1072 has two portions of differing diameters, thereby forming a ledge. When the piston 1042 is positioned in the housing 1028 (see FIGS. 38 and 39) the bore 1072 is in communication with the passage 1036.

A seal 1082 is provided at the first end 1030 of the housing 1028 and closes the main passage 1036 at that end. The seal 1082 is preferably mounted to the housing 1028 by an end cap 1083.

The seal 1082 is preferably a resilient, pre-slit re-sealable element. The end cap 1083 has an end with a passage 1085 therethrough which is aligned with the main passage 1036. A cylindrical side wall 1087 extends from the end of the cap 1083 and is arranged to engage the outside of the housing 1028 at the first end 1030. As illustrated, the cap 1083 has a groove on the inside of the wall 1087 which accepts a rib 1089 on the exterior of the housing 1028 in a snap-fit arrangement.

As with the previous embodiments, the branch passage 1038 is defined by a wall structure 1076 which extends outwardly from the main portion of the housing 1028. A sleeve 1078 is spaced outwardly from this wall structure 1076. Threads 1079 are positioned on the inside of the sleeve 1078.

The assembled valve 1020, wherein the piston 1042 is positioned in the main passage 1036 through the housing 1028, is best illustrated in FIGS. 38 and 39. As illustrated, the seal 1068 divides the main passage 1036 into a first chamber 1039 and a second chamber 1041. The first chamber 1039 comprises a space between the closed second end 1032 of the housing 1028, the second end 1052 of the piston 1042, and that space within the bore 1072 in the piston 1042. The second chamber 1041 is that space between the seal 1068 on the piston 1042 and the seal 1082 at the first end 1030 of the housing 1028.

As illustrated, the piston 1042 is moveable from a first or "uncompressed" position in which the shoulder 1062 engages the ledge 1048, to a second or "compressed" position in which the piston 1042 is moved towards the second end 1032 of the housing 1028.

Means are provided for biasing the piston 1042 into its first position. Preferably, this means comprises a spring 1070. As illustrated, the spring 1070 is a helical spring extending between the second end 1032 of the housing 1028 and the ledge formed in the piston 1042 by the changing diameter bore 1072.

The first chamber 1039 is air-filled. In order to accommodate the movement of the piston 1042 towards the second end 1032 of the housing 1028, an air vent 1075 is provided through the second end 1032.

The operation of the valve 1020 will now be described. A user first connects a first medical implement to the branch port 1035 in a manner as described above. The user then presses a blunt tip cannula or other medical implement 1037

(see FIG. 39) through the opening 1085 in the cap 1083, and then through the slit in the seal 1082. The user advances the implement 1037 until it presses the piston 1042 towards the second end 1032 of the housing 1028, as illustrated in FIG. 39.

When the piston 1042 is in this position, a flow path is established from the implement 1037 through the second chamber 1041 between the outside of the piston 1042 and the wall of the housing 1028 to the branch passage 1038. Fluid freely flows through the tip of the cannula 1037 because the open "V"-shaped spaced is provided below the tip at the first end 1050 of the piston 1052. In this position, the valve 1020 has a maximum fluid capacity V1.

When the user removes the cannula 1037, the pre-slit seal in the seal 1082 reseals, preventing fluid from flowing from the main passage 1026 out the first end 1030 of the valve 1020. At the same time, when the cannula 1037 or other implement is withdrawn, the piston 1042 moves upwardly to the position illustrated in FIG. 38 as a result of the spring force. When the piston 1042 is in the position illustrated in FIG. 38, the volume within the valve 1020 is at a minimum V2.

Because the fluid volume in the valve 1020 decreases as the piston 1042 moves upwardly, some fluid in the main passage 1026 is displaced. This fluid volume V1–V2 moves along the piston 1042 to the branch passage 1038.

This valve 1020 also has the advantage that flushing occurs at each use and the seal 1082 may be swabbed at its top surface to sterilize it.

A twelfth embodiment valve 1120 in accordance with the present invention is illustrated in FIGS. 49 and 50. The valve 1120 of this embodiment has a housing 1128 defining a main passage 1136 extending from a first end 1130 to a chamber 1141. A branch passage 1138 leads from the chamber 1141 generally perpendicular to the main passage 1136.

The housing 1128 has a second end 1132 opposite the first end 1130, the second end 1132 being open to the chamber 1141.

A seal 1182 is positioned within the chamber 1141. As illustrated, the seal 1182 is a resilient inverted "U"-shaped member. In a first position, the seal 1182 is arranged to close the branch passage 1138 from the chamber 1141 (see FIG. 49).

A piston 1142 is positioned within the main passage 1136 and rests upon a top portion of the seal 1182. As illustrated, the piston 1142 has a flat first end 1150 and a slanted second end 1152. The piston 1142 is generally cylindrical in cross-sectional shape.

The wall defining the main passage 1136 is cylindrical at the first end 1130 of the housing 1128. In a direction towards the second end 1132, the wall slants outward to define a sloped surface 1148.

A seal 1168 is preferably provided at the first end 1130 of the housing 1128. This seal 1168 is designed to seal against the outside of the piston 1142 to prevent fluid flow between the piston 1142 and housing 1128 at the first end 1130 of the valve 1120.

The operation of this valve 1120 is as follows. A user moves the tip of a cannula or other medical implement into engagement with the first end 1150 of the piston 1142. The user presses the piston 1142 towards the second end 1132 of the housing 1128 until the luer-lock connector or the like may be engaged with mating threads on the housing 1128, as illustrated in FIG. 50.

As the piston 1142 moves inwardly, because its tapered second end 1152 engages the seal 1182 and the seal collapses, the piston 1142 tips over against the sloped surface 1148 in the enlarged section of the main passage 1136. At this time, the top end 1150 of the piston 1142 is no longer a flat surface with respect to the end of the cannula. Thus, fluid is allowed to freely flow from the tip of the cannula.

As the piston 1142 moves inwardly, the seal 1182 compresses to a position in which the branch passage 1138 is in communication with the chamber 1141.

A fluid path is established from the cannula along the top end 1150 of the piston 1142, along the main passage 1136 into the chamber 1141, and then into the branch passage 1138. At this time, the fluid volume within the valve 1120 is an amount V1.

When the user withdraws the cannula, the seal 1182 presses the piston 1142 upwardly. The upward movement of the piston 1142 is facilitated by its engagement with the sloping surface 1148. Eventually, the seal 1182 moves the piston 1142 to the position illustrated in FIG. 49. At that time, the seal 1182 again seals the branch passage 1138 from the chamber 1141.

In addition, the seal 1168 seals around the piston 1142, preventing fluid from flowing from the inside of the valve 1120 through the main passage 1136 to the first end 1130, thus effecting a positive flow of fluid.

As the seal 1182 expands, the volume within the chamber 1141 is reduced, forcing fluid into the branch passage 1138.

Figure 52:
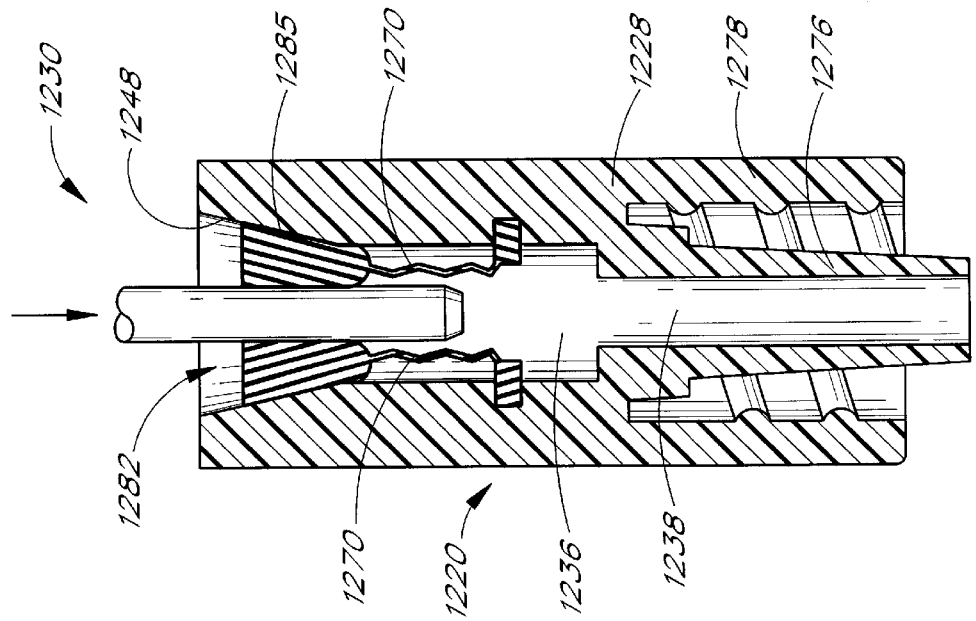
FIG. 52 is a cross-sectional view of the valve illustrated in FIG. 51 with the seal in a second position.
Figure 51:
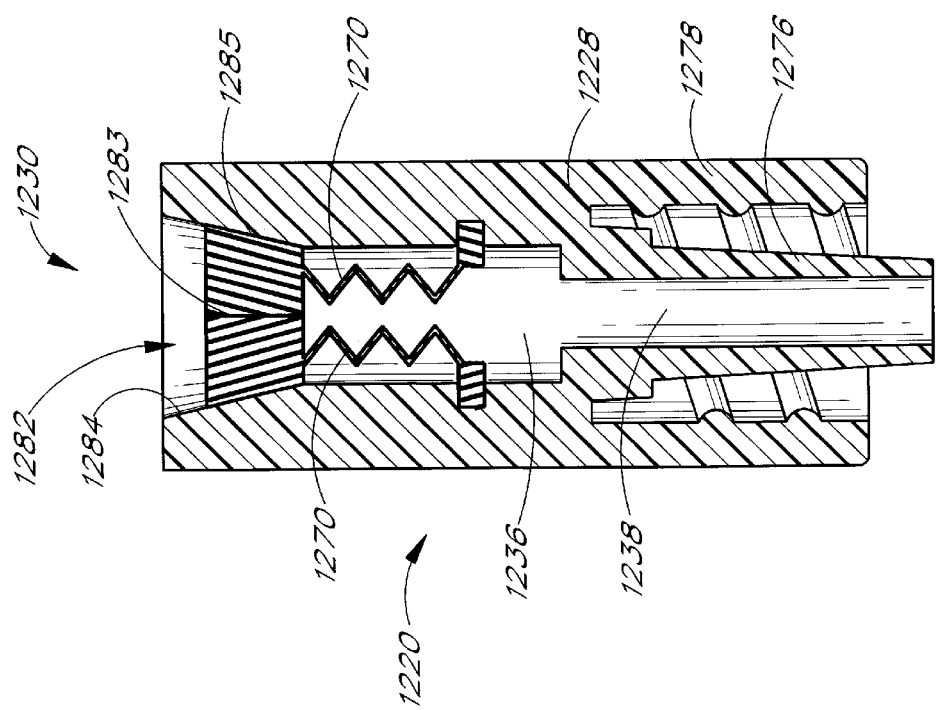
FIG. 51 is a cross-sectional view of a valve in accordance with a thirteenth embodiment of the present invention, illustrated with a seal thereof in a first position.

A thirteenth embodiment valve 1220 in accordance with the present invention is illustrated in FIGS. 51 and 52. This valve 1220 has a straight-flow arrangement similar to that of the valves illustrated in FIGS. 20–29.

The valve 1220 has a housing 1228 having a first end 1230 and second end 1232. A main passage 1236 extends from the first end 1230 to a smaller extension passage 1238 which extends to the second end 1232. The extension passage 1238 is primarily defined by a wall 1276 which is positioned within a sleeve 1278.

A seal 1282 is positioned in a conical portion 1248 of the main passage 1236 at the first end 1230. The seal 1282 preferably comprises first and second seal portions which, when put together, form an inverted frusto-conical shaped member. Each seal portion is generally semi-circular in cross-sectional shape (in a horizontal plane) and defines a flat inner surface 1283 for engagement with the other seal portion. The outside surface 1185 of each seal portion is curved, and tapers inwardly from top to bottom.

Each seal portion is biased in a direction towards the second end 1232 of the valve 1220. A resilient biasing member 1270 has a first end connected to a bottom surface of each seal portion and a second end secured to the housing 1228 some distance along the main passage 1236. As illustrated, each biasing member 1270 comprises a accordion-like elastic member.

Operation of the valve 1220 is as follows. When not in use, the biasing member 1270 corresponding to each portion of the seal 1282 biases the seal portions towards the second end 1232 of the valve 1220. In this position, the seal 1282 seals the main passage 1236 at the first end 1230 of the valve 1220.

A user inserts a cannula or other medical apparatus, as illustrated in FIG. 52, between the two portions of the seal 1282. As the user does this and advances the cannula, the seal portions must spread apart to accommodate the cannula. This causes the seal portions to move upwardly towards the first end 1230 of the valve 1220 along the conical surface 1248 against the force of the biasing member 1270.

Once the cannula is inserted, a fluid path is established therefrom through the main passage 1236 and extension passage 1238 through the valve 1230. At this time the fluid volume within the valve 1220 is an amount V1.

When the user withdraws the cannula, the fluid volume in the valve 1220 reduces to an amount V2, causing fluid to be displaced through the extension passage 1238. In particular, once the cannula is removed, the biasing members 1270 draw the seal portions back towards the second end 1232 of the valve 1230 to the position illustrated in FIG. 51. The seal 1282 in this position reseals the main passage 1236 at the first end 1230 of the valve 1220.

The valves described above having a seal (182, 282, 382, 482, 582, 682, 782, 882, 982, 1082, 1168, 1282) may be adapted for use with a needle or other implement instead of the blunt cannula 37 illustrated. In this arrangement, the seal may be solid (i.e., not pre-slit). In that case, the piston 142 (or similar member in the later described embodiments) is preferably constructed of a durable material which is not ready penetrated by the needle.

As described above, each valve is preferably provided with a means for opening and closing a fluid path through the valve. In at least one embodiment, this means is a moveable piston (ex. piston 42, FIG. 12) while in other embodiments it is a pre-slit seal (ex. seal 182, FIG. 19). Those of skill in the art will appreciate that a variety of means may be provided in addition to those described. For example, a resealable septum or the like may be used.

In addition, each valve includes a means for decreasing the fluid volume therein when one of the medical implements is disconnected, for producing a positive fluid flow. In some embodiments this means is a piston (ex. piston 42, FIG. 12 or piston 1042, FIG. 38) while in other embodiments it is a resilient member such as a diaphragm or foam-like element (ex. element 670, FIG. 28 or element 770, FIG. 30). Those of skill in the art will appreciate that other means may be provided.

In some instances, the means for opening and closing the fluid path is the same as the means for decreasing the fluid volume (ex. piston 42, FIG. 12).

In the embodiments described above, the fluid space inside the valve increases upon insertion of a medical implement in the compressed state and decreases upon withdrawal of the medical implement in the decompressed state. In some embodiments, the structure defining the fluid space is substantially relaxed and does not store substantial amount of potential energy. Insertion of the medical implement causes a change in the structure that allows it to store potential energy. The potential energy is released upon withdrawal of the medical implement and the structure returns to a substantially relaxed condition.

The above presents a description of the best mode contemplated of carrying out the present invention, and of the manner and process of using it, in such full, clear, concise, and exact terms as to enable any person skilled in the art to which it pertains to make and use this invention. This invention is, however, susceptible to modifications and alternate constructions from that discussed above which are fully equivalent. The embodiments described are meant to be illustrative and not exhaustive. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A medical valve for controlling the flow of fluid between a first medical implement and a second medical implement, said valve comprising a body having a cavity in communication with a second medical implement and an opening adapted to receive a first medical implement, a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said sealing element comprising a piston movably mounted with respect to said body, and a ledge positioned within said cavity, said piston having a shoulder engaging said ledge when said piston is in said first position.

2. The medical valve in accordance with claim 1, including means for biasing said piston into said first position.

3. The medical valve in accordance with claim 2, wherein said means for biasing comprises a spring.

4. A medical valve for controlling the flow of fluid between a first medical implement and a second medical implement, said valve comprising a body having a cavity in communication with a second medical implement and an opening adapted to receive a first medical implement, and a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said sealing element comprising a piston movably mounted with respect to said body, said piston dividing said cavity into a first fluid filled chamber and a second, air-filled chamber.

5. The medical valve in accordance with claim 4, further including a vent through said body extending to said air-filled chamber.

6. The medical valve in accordance with claim 4, wherein said piston includes a hollow recess in communication with said air-filled chamber.

7. A medical valve for controlling the flow of fluid between a first medical implement and a second medical implement, said valve comprising a body having a cavity in communication with a second medical implement and an opening adapted to receive a first medical implement, and a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said sealing element comprising a piston movably mounted with respect to said body, said piston having a head for engagement by said first medical implement, said head having a slanted surface.

8. A medical valve for controlling the flow of fluid between a first medical implement and a second medical implement, said valve comprising a body having a cavity in communication with a second medical implement and an opening adapted to receive a first medical implement, and a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said opening being at a first end of said body, said body having a closed second end and a branch, said branch defining a branch passage leading from said cavity.

9. A medical valve for controlling the flow of fluid between a first medical implement and a second medical implement, said valve comprising a body having a cavity in communication with a second medical implement and an opening adapted to receive a first medical implement, a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, a piston member movably positioned with in said body, and means for biasing said piston member in the direction of said sealing element, said means for biasing comprising a member cooperating with said body to define an air-filled chamber.

10. A medical valve for controlling the flow of fluid between a first medical implement and a second medical implement, said valve comprising a body having a cavity in communication with a second medical implement and an opening adapted to receive a first medical implement, a rigid sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, a piston member movably positioned within said body, and means for biasing said piston member in the direction of said sealing element, said means for biasing comprising an air-filled member.

11. A medical valve for controlling the flow of fluid between a first medical implement and a second medical implement, said valve comprising a body having a cavity in communication with a second medical implement, an opening adapted to receive a first medical implement, and a sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said sealing element comprising a piston movably mounted with respect to said body, said piston having a head for engagement by said first medical implement, said head having a slanted surface.

12. A medical valve for controlling the flow of fluid between a first medical implement and a second medical implement, said valve comprising a body having a cavity in communication with a second medical implement, an opening adapted to receive a first medical implement, and a sealing element positioned within said body and movable between a first position in which said seal prevents fluid flow through said body and a second position in which fluid flow is permitted through said body, said cavity including a fluid space which automatically and reversibly increases in size when said first medical implement is connected to said valve and which contracts in size when said first medical implement is disconnected, said sealing element comprising a piston movably mounted with respect to said body, said piston dividing said cavity into a first fluid filled chamber and a second, air-filled chamber, said piston including a hollow recess in communication with said air-filled chamber.

* * * * *